(12) United States Patent
Breder et al.

US007943173B2

(10) Patent No.: US 7,943,173 B2
(45) Date of Patent: May 17, 2011

(54) PHARMACEUTICAL COMBINATIONS OF OXYCODONE AND NALOXONE

(75) Inventors: Christopher D. Breder, Greenwich, CT (US); Robert D. Colucci, Newtown, CT (US); Stephen A Howard, Danbury, CT (US); Benjamin Oshlack, New York, NY (US); Curtis Wright, Norwalk, CT (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 10/199,972

(22) Filed: Jul. 18, 2002

(65) Prior Publication Data

US 2003/0069263 A1 Apr. 10, 2003

Related U.S. Application Data

(60) Provisional application No. 60/306,301, filed on Jul. 18, 2001.

(51) Int. Cl.
*A61K 9/14* (2006.01)
*A61K 9/22* (2006.01)
*A61K 9/57* (2006.01)
(52) U.S. Cl. .................. 424/484; 424/457; 424/468
(58) Field of Classification Search .................. 424/422, 424/423, 451, 452, 457, 464, 465, 468, 489; 514/282, 289
See application file for complete search history.

(56) References Cited

U.S. PATENT DOCUMENTS

| | | | |
|---|---|---|---|
| 2,770,569 A | 11/1956 | Fromherz et al. ............... 167/65 |
| 3,133,132 A | 5/1964 | Loeb et al. ...................... 264/49 |
| 3,173,876 A | 3/1965 | Zobrist ......................... 252/137 |
| 3,276,586 A | 10/1966 | Rosaen .......................... 210/90 |
| 3,332,950 A | 7/1967 | Blumberg et al. ............. 260/285 |
| 3,493,657 A | 2/1970 | Lewenstein et al. .......... 424/260 |
| 3,541,005 A | 11/1970 | Strathmann et al. ........... 210/19 |
| 3,541,006 A | 11/1970 | Bixler et al. ................... 210/23 |
| 3,676,557 A | 7/1972 | Lachman et al. ............. 424/260 |
| 3,773,955 A | 11/1973 | Pachter et al. ................ 424/260 |
| 3,879,555 A | 4/1975 | Pachter et al. ................ 424/260 |
| 3,916,899 A | 11/1975 | Russell ...................... 128/145.8 |
| 3,965,256 A | 6/1976 | Leslie ............................ 424/22 |
| 3,966,940 A | 6/1976 | Pachter et al. ................ 424/260 |
| 4,160,020 A | 7/1979 | Ayer et al. ....................... 424/15 |
| 4,175,119 A | 11/1979 | Porter ............................ 424/10 |
| 4,176,186 A | 11/1979 | Goldberg ..................... 424/260 |
| 4,200,098 A | 4/1980 | Ayer et al. .................... 128/260 |
| 4,237,140 A | 12/1980 | Dudzinski .................... 424/260 |
| 4,285,987 A | 8/1981 | Ayer et al. ....................... 427/3 |
| 4,366,310 A | 12/1982 | Leslie ............................ 536/56 |
| 4,401,672 A | 8/1983 | Portoghese et al. .......... 424/260 |
| 4,443,428 A | 4/1984 | Oshlack et al. ................. 424/22 |
| 4,451,470 A | 5/1984 | Ganti ............................ 424/260 |
| 4,457,933 A * | 7/1984 | Gordon et al. ................ 514/282 |
| 4,464,378 A | 8/1984 | Hussain et al. ............... 424/260 |
| 4,573,995 A | 3/1986 | Chen et al. .................... 604/896 |
| 4,582,835 A | 4/1986 | Lewis et al. ................... 514/282 |
| 4,587,118 A | 5/1986 | Hsiao ............................ 424/459 |
| 4,608,376 A | 8/1986 | Pasternak ..................... 514/282 |
| 4,661,492 A | 4/1987 | Lewis et al. ................... 514/282 |
| 4,719,215 A | 1/1988 | Goldberg ...................... 514/282 |
| 4,730,048 A | 3/1988 | Portoghese et al. ............ 546/45 |
| 4,760,069 A | 7/1988 | Rzeszotarski et al. ........ 514/282 |
| 4,769,372 A * | 9/1988 | Kreek ........................... 514/282 |
| 4,785,000 A | 11/1988 | Kreek et al. .................. 514/282 |
| 4,803,208 A | 2/1989 | Pasternak ..................... 514/282 |
| 4,806,341 A | 2/1989 | Chien et al. ................... 424/448 |
| 4,806,543 A | 2/1989 | Choi ............................. 514/464 |
| 4,806,558 A | 2/1989 | Wuest et al. .................. 514/381 |
| 4,828,836 A | 5/1989 | Elger et al. ................... 424/419 |
| 4,834,965 A | 5/1989 | Martani et al. ............... 424/488 |
| 4,834,984 A | 5/1989 | Goldie et al. ................. 424/488 |
| 4,834,985 A | 5/1989 | Elger et al. ................... 424/488 |
| 4,844,907 A | 7/1989 | Elger et al. ................... 424/465 |
| 4,844,909 A | 7/1989 | Goldie et al. ................. 424/480 |
| 4,844,910 A | 7/1989 | Leslie et al. .................. 424/494 |
| 4,861,598 A | 8/1989 | Oshlack et al. ............... 424/468 |
| 4,861,781 A | 8/1989 | Goldberg ...................... 514/282 |
| 4,867,985 A | 9/1989 | Heafield et al. .............. 424/461 |
| 4,873,076 A | 10/1989 | Fishman et al. ................ 412/10 |
| 4,882,335 A | 11/1989 | Sinclair ........................ 514/282 |
| 4,889,860 A | 12/1989 | Rzeszotarski et al. ........ 514/282 |
| 4,935,428 A | 6/1990 | Lewis ........................... 514/282 |
| 4,940,587 A | 7/1990 | Jenkins et al. ................ 424/480 |
| 4,970,075 A | 11/1990 | Oshlak ......................... 424/451 |
| 4,987,136 A | 1/1991 | Kreek et al. .................. 514/282 |
| 4,990,341 A | 2/1991 | Goldie et al. ................. 424/484 |
| 5,071,646 A | 12/1991 | Malkowska et al. .......... 424/497 |
| 5,075,341 A | 12/1991 | Mendelson et al. .......... 514/282 |
| 5,086,058 A | 2/1992 | Sinclair et al. ............... 514/282 |
| 5,091,189 A | 2/1992 | Heafield et al. .............. 424/457 |
| 5,096,715 A | 3/1992 | Sinclair ........................ 424/449 |
| 5,102,887 A | 4/1992 | Goldberg ...................... 514/282 |
| 5,130,311 A | 7/1992 | Guillaumet et al. ........ 514/234.2 |
| 5,149,538 A | 9/1992 | Granger et al. ............... 424/449 |
| 5,215,758 A | 6/1993 | Krishnamurthy ............. 424/488 |
| 5,225,440 A | 7/1993 | London et al. ................ 514/535 |
| 5,226,331 A | 7/1993 | Thompson et al. ........... 73/865.9 |
| 5,236,714 A | 8/1993 | Lee et al. ....................... 424/449 |
| 5,256,669 A | 10/1993 | Askanazi et al. ............. 514/282 |
| 5,266,331 A | 11/1993 | Oshlak et al. ................ 424/468 |
| 5,273,760 A | 12/1993 | Oshlak et al. ................ 424/486 |
| 5,286,493 A | 2/1994 | Oshlak et al. ................ 424/468 |

(Continued)

FOREIGN PATENT DOCUMENTS

DE 2222039 11/1972

(Continued)

OTHER PUBLICATIONS

Philip D. Kanof et al., "Levels of Opioid Physical Dependence in Heroin Addicts," Drug and Alcohol Dependence, 27 (1991) 253-262.

(Continued)

*Primary Examiner* — S. Tran
(74) *Attorney, Agent, or Firm* — Davidson, Davidson & Kappel LLC

(57) ABSTRACT

Disclosed in certain embodiments is a pharmaceutical composition comprising from 10 to 40 mg of oxycodone or a pharmaceutically acceptable salt thereof and 0.65 to 0.90 mg naloxone or a pharmaceutically acceptable salt thereof.

38 Claims, 6 Drawing Sheets

U.S. PATENT DOCUMENTS

| | | | |
|---|---|---|---|
| 5,316,759 A | 5/1994 | Rose et al. | 424/10 |
| 5,317,022 A | 5/1994 | Borsodi et al. | 514/282 |
| 5,321,012 A | 6/1994 | Mayer et al. | 514/25 |
| 5,324,351 A | 6/1994 | Oshlak et al. | 106/153 |
| 5,336,691 A | 8/1994 | Raffa et al. | 514/629 |
| 5,352,680 A | 10/1994 | Portoghese et al. | 514/279 |
| 5,352,683 A | 10/1994 | Mayer et al. | 514/289 |
| 5,356,467 A | 10/1994 | Oshlak et al. | 106/153 |
| 5,356,900 A | 10/1994 | Bihari et al. | 514/282 |
| 5,376,662 A | 12/1994 | Ockert | 514/282 |
| 5,409,944 A | 4/1995 | Black et al. | 514/359 |
| 5,411,745 A | 5/1995 | Oshlack et al. | 424/456 |
| 5,411,965 A * | 5/1995 | Reid et al. | 514/279 |
| 5,426,112 A | 6/1995 | Zagon et al. | 514/282 |
| 5,436,265 A | 7/1995 | Black et al. | 514/420 |
| 5,457,208 A | 10/1995 | Portoghese et al. | 546/35 |
| 5,460,826 A | 10/1995 | Merrill et al. | 424/470 |
| 5,472,712 A | 12/1995 | Oshlack et al. | 424/480 |
| 5,472,943 A | 12/1995 | Crain et al. | 514/12 |
| 5,474,995 A | 12/1995 | Ducharme et al. | 514/241 |
| 5,478,577 A | 12/1995 | Sackler et al. | 424/489 |
| 5,486,362 A | 1/1996 | Kitchell et al. | 424/426 |
| 5,500,227 A | 3/1996 | Oshlack et al. | 424/476 |
| 5,502,058 A | 3/1996 | Mayer et al. | 514/289 |
| 5,508,042 A | 4/1996 | Oshlack et al. | 424/468 |
| 5,508,043 A | 4/1996 | Krishnamurthy | 424/484 |
| 5,510,368 A | 4/1996 | Lau et al. | 514/419 |
| 5,512,578 A | 4/1996 | Crain et al. | 514/282 |
| 5,514,680 A | 5/1996 | Weber et al. | 514/249 |
| 5,521,213 A | 5/1996 | Prasit et al. | 514/443 |
| 5,534,492 A | 7/1996 | Aston et al. | 514/608 |
| 5,536,752 A | 7/1996 | Ducharme et al. | 514/602 |
| 5,549,912 A | 8/1996 | Oshlack et al. | 424/468 |
| 5,550,142 A | 8/1996 | Ducharme et al. | 514/365 |
| 5,552,406 A * | 9/1996 | Mendelson et al. | 514/279 |
| 5,552,422 A | 9/1996 | Gauthier et al. | 514/368 |
| 5,556,838 A | 9/1996 | Mayer et al. | 514/25 |
| 5,574,052 A | 11/1996 | Rose et al. | 514/343 |
| 5,578,725 A | 11/1996 | Portoghese et al. | 546/35 |
| 5,580,876 A | 12/1996 | Crain et al. | 514/282 |
| 5,585,348 A | 12/1996 | Crain et al. | 514/12 |
| 5,591,452 A | 1/1997 | Miller et al. | 424/468 |
| 5,593,994 A | 1/1997 | Batt et al. | 514/252 |
| 5,601,845 A | 2/1997 | Buxton et al. | 424/495 |
| 5,604,253 A | 2/1997 | Lau et al. | 514/415 |
| 5,604,260 A | 2/1997 | Guay et al. | 514/605 |
| 5,616,601 A | 4/1997 | Khanna et al. | 514/399 |
| 5,622,722 A | 4/1997 | Knott et al. | 424/494 |
| 5,624,932 A | 4/1997 | Qin et al. | 514/282 |
| 5,633,259 A | 5/1997 | Qin et al. | 514/282 |
| 5,639,476 A | 6/1997 | Oshlack et al. | 424/468 |
| 5,639,780 A | 6/1997 | Lau et al. | 514/419 |
| 5,656,295 A | 8/1997 | Oshalck et al. | 424/468 |
| 5,670,172 A | 9/1997 | Buxton et al. | 424/495 |
| 5,672,360 A | 9/1997 | Sackler et al. | 424/490 |
| 5,681,585 A | 10/1997 | Oshlack et al. | 424/494 |
| 5,763,452 A | 6/1998 | Miller et al. | 514/282 |
| 5,767,125 A | 6/1998 | Crain et al. | 514/282 |
| 5,780,051 A * | 7/1998 | Eswara et al. | 424/449 |
| 5,780,479 A | 7/1998 | Kim | 514/282 |
| 5,811,126 A | 9/1998 | Krishnamurthy | 424/498 |
| 5,834,477 A | 11/1998 | Mioduszewski | 514/282 |
| 5,843,480 A | 12/1998 | Miller et al. | 424/484 |
| 5,849,240 A | 12/1998 | Miller et al. | 264/460 |
| 5,858,017 A | 1/1999 | Demopulos et al. | 604/890.1 |
| 5,860,950 A | 1/1999 | Demopulos et al. | 604/49 |
| 5,866,164 A | 2/1999 | Kuczynski et al. | 424/472 |
| 5,869,097 A | 2/1999 | Wong et al. | 424/473 |
| 5,879,705 A | 3/1999 | Heafield et al. | 424/464 |
| 5,880,132 A | 3/1999 | Hill | 514/282 |
| 5,891,471 A | 4/1999 | Miller et al. | 424/468 |
| 5,908,848 A | 6/1999 | Miller et al. | 514/282 |
| 5,942,241 A | 8/1999 | Chasin et al. | 424/426 |
| 5,958,452 A | 9/1999 | Oshlack et al. | 424/457 |
| 5,958,459 A | 9/1999 | Chasin et al. | 424/490 |
| 5,965,161 A | 10/1999 | Oshlack et al. | 424/457 |
| 5,965,163 A | 10/1999 | Miller et al. | 424/468 |
| 5,968,547 A | 10/1999 | Reder et al. | 424/449 |
| 5,968,551 A | 10/1999 | Oshlack et al. | 424/456 |
| 5,972,954 A | 10/1999 | Foss | 514/282 |
| 5,998,434 A | 12/1999 | Mitch et al. | 514/210.16 |
| 6,004,970 A | 12/1999 | O'Malley et al. | |
| 6,024,982 A | 2/2000 | Oshlack et al. | 424/476 |
| 6,068,855 A | 5/2000 | Leslie et al. | 424/468 |
| 6,077,532 A | 6/2000 | Malkowska et al. | 424/457 |
| 6,077,533 A | 6/2000 | Oshlack et al. | 424/461 |
| 6,096,756 A | 8/2000 | Crain et al. | 514/282 |
| 6,103,258 A | 8/2000 | Simon | 424/449 |
| 6,103,261 A | 8/2000 | Chasin et al. | 424/459 |
| 6,120,806 A | 9/2000 | Whitmire | |
| 6,143,322 A | 11/2000 | Sackler et al. | 424/459 |
| 6,143,328 A | 11/2000 | Heafield et al. | 424/489 |
| 6,162,467 A | 12/2000 | Miller et al. | 424/468 |
| 6,194,382 B1 | 2/2001 | Crain et al. | 514/2 |
| 6,210,714 B1 | 4/2001 | Oshlack et al. | 424/476 |
| 6,228,863 B1 | 5/2001 | Palermo et al. | 514/282 |
| 6,254,887 B1 | 7/2001 | Miller et al. | 424/468 |
| 6,258,379 B1 * | 7/2001 | Weinstein et al. | 424/451 |
| 6,261,599 B1 | 7/2001 | Oshlack et al. | 424/457 |
| 6,274,591 B1 | 8/2001 | Foss et al. | |
| 6,277,384 B1 | 8/2001 | Kaiko et al. | 424/400 |
| 6,294,195 B1 | 9/2001 | Oshlack et al. | 424/457 |
| 6,306,438 B1 | 10/2001 | Oshlack et al. | 424/468 |
| 6,326,027 B1 | 12/2001 | Miller et al. | 424/468 |
| 6,335,033 B2 | 1/2002 | Oshlack et al. | 424/457 |
| 6,362,194 B1 | 3/2002 | Crain et al. | 514/285 |
| 6,375,957 B1 | 4/2002 | Kaiko et al. | 424/400 |
| 6,387,404 B2 | 5/2002 | Oshlack et al. | 424/480 |
| 6,395,705 B2 | 5/2002 | Crain et al. | 514/2 |
| 6,399,096 B1 | 6/2002 | Miller et al. | 424/464 |
| 6,451,806 B2 * | 9/2002 | Farrar | 514/282 |
| 6,475,494 B2 | 11/2002 | Kaiko et al. | 424/400 |
| 6,552,031 B1 | 4/2003 | Burch et al. | |
| 6,627,635 B2 | 9/2003 | Palermo et al. | 514/282 |
| 6,696,066 B2 | 2/2004 | Kaiko et al. | 424/400 |
| 6,696,088 B2 * | 2/2004 | Oshlack et al. | 424/465 |
| 6,716,449 B2 | 4/2004 | Oshlack et al. | 424/449 |
| 6,765,010 B2 | 7/2004 | Crain et al. | |
| 7,144,587 B2 | 12/2006 | Oshlack et al. | |
| 7,172,767 B2 | 2/2007 | Kaiko et al. | |
| 7,332,182 B2 | 2/2008 | Sackler | |
| 2001/0006967 A1 | 7/2001 | Crain et al. | 514/253.04 |
| 2001/0008639 A1* | 7/2001 | Oshlack et al. | 424/468 |
| 2001/0018413 A1 | 8/2001 | Crain et al. | 514/2 |
| 2002/0058673 A1 | 5/2002 | Kaiko et al. | |
| 2003/0004177 A1* | 1/2003 | Kao et al. | 514/282 |
| 2003/0068371 A1 | 4/2003 | Oshlack et al. | |
| 2003/0073714 A1 | 4/2003 | Breder et al. | |
| 2003/0157168 A1 | 8/2003 | Breder et al. | |
| 2003/0191147 A1 * | 10/2003 | Sherman et al. | 514/282 |
| 2003/0207905 A1* | 11/2003 | Levine | 514/282 |
| 2004/0092542 A1 | 5/2004 | Oshlack et al. | |
| 2004/0186121 A1 | 9/2004 | Oshlack et al. | |
| 2004/0192715 A1 | 9/2004 | Chasin et al. | |
| 2004/0228924 A1 | 11/2004 | Oshlack et al. | |
| 2005/0095291 A1 | 5/2005 | Oshlack et al. | |
| 2005/0181046 A1 | 8/2005 | Oshlack et al. | |
| 2005/0245483 A1 | 11/2005 | Brogmann et al. | |
| 2005/0245556 A1 | 11/2005 | Brogmann et al. | |
| 2005/0245557 A1 | 11/2005 | Schoenhard et al. | |
| 2006/0039970 A1 | 2/2006 | Oshlack et al. | |
| 2006/0182801 A1 | 8/2006 | Breder et al. | |
| 2006/0194826 A1 | 8/2006 | Oshlack et al. | |
| 2007/0014732 A1 | 1/2007 | Sackler | |
| 2007/0122348 A1 | 5/2007 | Kaiko et al. | |
| 2008/0020028 A1 | 1/2008 | Shevchuk et al. | |

FOREIGN PATENT DOCUMENTS

| | | |
|---|---|---|
| DE | 4325465 | 2/1995 |
| DE | 29719704 | 11/1997 |
| DE | 19651551 | 6/1998 |
| EP | 0193355 A3 | 9/1986 |
| EP | 0205282 | 12/1986 |
| EP | 0319243 A1 | 6/1989 |
| EP | 0352361 | 1/1990 |
| EP | 0319243 A2 | 11/1990 |
| EP | 0647448 | 4/1995 |

| | | |
|---|---|---|
| EP | 0913152 | 6/1999 |
| EP | 0548448 B1 | 9/2000 |
| EP | 0759303 | 10/2002 |
| JP | S59-51223 | 3/1984 |
| JP | H10-338634 | 12/1998 |
| WO | 8303197 | 9/1983 |
| WO | 8701282 | 3/1987 |
| WO | 9004965 | 5/1990 |
| WO | 9406426 | 3/1994 |
| WO | 9503804 | 2/1995 |
| WO | WO 95/28963 | 11/1995 |
| WO | 9602251 | 2/1996 |
| WO | 9733566 | 9/1997 |
| WO | WO9825613 | 6/1998 |
| WO | 9835679 | 8/1998 |
| WO | 9932120 | 7/1999 |
| WO | WO 99/32119 | 7/1999 |
| WO | WO 99/32120 | 7/1999 |
| WO | WO 9932120 A1 * | 7/1999 |
| WO | 0001377 | 1/2000 |
| WO | WO0038649 | 7/2000 |
| WO | 0051592 | 9/2000 |
| WO | WO 00/54774 | 9/2000 |
| WO | 0067739 | 11/2000 |
| WO | 0132180 A2 | 5/2001 |
| WO | 0137785 A2 | 5/2001 |
| WO | 0152851 A1 | 7/2001 |
| WO | 0158477 | 8/2001 |
| WO | 0168080 A2 | 9/2001 |
| WO | 0185150 | 11/2001 |
| WO | 0185257 A2 | 11/2001 |
| WO | 0193852 A2 | 12/2001 |
| WO | 2004052346 A1 | 6/2004 |

OTHER PUBLICATIONS

J.E. Peachey et al., "Assessment of Opioid Dependence with Naloxone," British Journal of Addiction (1988) 83(2), 193-201.

John G. Nutt et al., "Methadone-naloxone Mixtures for Use in Methadone Maintenance Prograpms," Clinical Pharmacology and Therapeutics, vol. 15, No. 2, pp. 156-166, received for publication Jun. 11, 1973.

Richard I. H. Wang et al., "Rating the Presence and Severity of Opiate Dependence," Clinical Pharmacology and Therapeutics, vol. 16, No. 4, pp. 653-657; received for publication Jan. 21, 1974.

Richard B. Resnick et al., "Naloxone Precipitated Withdrawal: A Method for Rapid Induction Onto Naltrexone," Clinical Pharmacology and Therapeutics, vol. 21, No. 4, pp. 409-413; received for publication Nov. 16, 1976.

Barbara A. Judson et al., "The Naloxone Test Opiate Dependence," Clin. Pharmacol. Ther., vol. 27, No. 4, pp. 492-501, received for publication Sep. 15, 1979.

Philip D. Kanof et al., "Clinical Characteristics of Naloxone-Precipitated Withdrawal in Human Opioid-Dependent Subjects," The Journal of Pharmacology and Experimental Therapeutics, vol. 260, No. 1, pp. 355-363, 1992.

Richard L. Wiesen et al., "The Safety and Value of Naloxone as a Therapeutic Aid," Drug and Alcohol Dependence, 2 (1977) pp. 123-130.

"Field of Chemical Therapy," 1998, vol. 14, No. 6, pp. 86-88.

Foss, J.F., et al.Abstract, "Prevention of Apomorphine- or Cisplatin-induced emesis in the dog by combination of Methylnaltrexone and Morphine",Cancer Chemother Pharmacol (1998); 42(4):287-91.

Yuan et al., "Efficacy of Orally Administered Methylnaltrexone in Decreasing Subjective Effects After Intravenous Morphine",Drug and Alcohol Dependence (1998); 52:161-165.

Gan et al., "Opioid-Sparing Effects of a Low-Dose Infusion of Naloxone in Patient-Administered Morphine Sulfate," Anesthesiology (1997), 87(5):1075-1080.

Shen et al., "Ultra-Low Doses of Naltrexone or Etorphine Increase Morphine's Antinocieceptive Potencey and Attenuate Tolerance/Dependence in Mice," Brain Research (1997), 757:176-190.

Yuan et al., "The Safety and Efficacy of Oral Methylnaltrexone in Preventing Morphine-induced Delay in Oral-Cecal Transit Time", Clinical Trials and Therapeutics (1997), 61:467-475.

Mendelson J., et al, "Buprenorphine and Naloxone Interactions in Opiate Dependent Volunteers" Clin. Phar. Ther. (1996), 60:105-114.

Walsh et al., "Effects of Naltrexone on Response to Intravenous Cocain, Hydromorphone and their Combination in Humans," (1996).

Chih-Cheng Chien, et al., "Sigma Antagonists Potentiate Opioid Analgesia in Rats", Neuroscience Letters 190 (1995), 137-139.

Crain et al., "Ultra-Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995) 92:10540-10544.

Hanson, Analgesic, Antipyretic and Anti-Inflammatory Drugs in Remington's Science and Practice of Pharmacy (1995), 2:1207.

Talwin NX, Physician's Desk Reference $48^{th}$ Ed. (1994) Montvale, NJ 2120-2121.

Foss et al., "Dose related Antagonism of the Emetic Effect of Morphine by Methylnaltrexone in Dogs",J. Clin Pharmacol (1993), 33:747-751.

Holmes et al., "Inhibiting Spinal Dynorphin A Component Enhances Intrathecal Morphine Antinociception in Mice", Anesth. Analg. (1993), 77:1166-73.

Miakowski et al., "Inhibition of Spinal Opioid Analgesia by Supraspinal Administration of Selective Opioid Antagonists", Brain Research (1992), 30:263-274.

Weinhold et al., "Buprenorphine Alone and in Combination with Naltrexone in Non-Dependent Humans," Drug and Alcohol Dependence (1992), 30:263-274.

Cappel et al., "Enhancement of Naloxone Induced Analgesia by Pretreatment with Morphine" Pharma. Bioch. & Behav. (1989), 34:425-427.

Vaccarino et al.,"Analgesia Produced by Normal Doses of Opioid Antagonists Alone and in Combination with Morphine", Pain (1989), 36:103-109.

Gonzalez et al., "Naltrexone: A Review of its Pharmacodynamic and Pharmacokinetic Properties and Therapeutic Efficacy in the Management of Opioid Dependence," Drugs (1988), 35:192-213.

Sunshine, et al., "Analgesic Efficacy of Pentazocine Versus a Pentazocine-Naloxone Combination Following Oral Administration," Clin. J. Pain (1988), 4:35-40.

Wang et al., "Crossover and Parallel Study of Oral Analgesics," J. Clin. Pharmacol (1981), 21:162-168.

Alavrez-Fuentes, et al. "Effectiveness of Repeated Administration of a New Ora Naltrexone Controlled-Release System in Morphine Analgesia"; J. Pharm Pharmcaol (2001), 53:1201-1205.

Alvarez-Fuentes, et al., :Preclinical Study of an Oral Controlled Release Naltrexone Complex in Mice; J. Pharm Pharmacol (2000), 52:659-663.

Archer, Sydney; "Historical Perspective on the Chemistry and Development of Naltrexone"; Naltrexone Research Monograph28 (1980) p. 3-9.

Baum et al., "The Impact of the Addition of Naloxone on thr Use and Abuse of Pentazocine"; Public Health Reports (1987) vol. 102, No. 4 p. 426-429.

Rapaka et al., "Discovery of Novel Opioid Medications"; NIDA Research Monograph 147 (1995) p. 55-83.

Bloom et al., "Clinical Studies with Naloxone/Methadone in a Ratio of 1:20"; $5^{th}$ National Conference on Methadone Treatment (1973) vol. 2, p. 1342-1349.

Briscoe et al., "Methoclocinnamox: Time Course of Changes in Alfetnanil-Reinforced Rhesus Monkeys"; Psychopharmacology (2000) 148:393-399.

Abstract of Bromm, et al., "A Sensitive Method to Evaluate Effects of Analgesics in Man"; Meth and Find Exptl Clin Pharmacol 5 (8) (1983) p. 545-551.

Bullingham et al., "Clinical Pharamcokinetics of Narcotic Agonist-Antagonist Drugs"; Clinical Pharm (1983) 8: 332-343.

Calimlim, et al. "Effect of Naloxone on the Analgesic Activity of Methadone in a 1:10 Oral Combination"; Clin Pharmacol and There (1974) vol. 15; No. 6 pp. 556-564.

Chemy, Nathan I., "Opioid Analgesics"; Drugs (May 1996):51 (5) pp. 713-737.

Chiang, et al. "Clinical Evaluation of a Naltrexone Sustained-Release Preparation"; Drug and Alcohol Dependence (1985) 16, pp. 1-8.

Chiang et al., "Kinetics of a Naltrexone Sustained-Release Preparation"; Clin Pharmacol Thera (1984) vol. 36 No. 5, pp. 704-708.

Comer et al., "Depot Naltrexone: Long-lasting Antagonism of the Effects of Heroin un Humans"; Psychopharmacology (2002) 159, pp. 351-360.

Crabtree et al., "Review of Naltrexone, a long-acting Opiate Antagonist"; Clinical Pharmacy, vol. 3 (1984) pp. 273-280.

Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 82 (1999)pp. 1-11.

Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 84 (2000) pp. 121-131.

Fishman et al., "Disposition of Naloxone-7,8-$^3$H in Normal & Narcotic Dependent Men"; J. Pharm. and Exper. Thera (1973)vol. 10 No. 2;pp. 575-580.

Fraser, Albert D., et al., "Clinical Toxicology of Drugs Used in the Treatment of Opiate Dependency"; Clinical Toxicology I (1990) vol. 10, No. 2; pp. 375-386.

Freye et al., effects of Tramadol and Tilidine/Naloxone on Oral-Caecal Transit & Pupillary light Reflex; Arzneim-Forsch/Drug Res. 50(I)(2000)pp. 24-30.

Fudala, et al., "Effects of Buprenorphine asnd Naloxone in Morphine-Stabilized Opioid Addicts"; Drug and Alcohol Dependence 50 (1998) pp. 1-8.

Fudala et al., "Human Pharmacology and Abuse Potential of Nalmefene"; Clin Pharm and Thera (1991) vol. 49, 3, pp. 300-306.

Gal et al., "Prolonged Blockade of Opioid Effect with Oral Nalmefene"; Clin Pharm and Thera (1986) pp. 537-542.

Gerra et al., "Clonidine and Opiate Receptor Antagonists in the Treatment of Heroin Addiction"; J. Substance Abuse Treatment (1995) vol. 12, 1, pp. 35-41.

Ghodse, et al., "Opioid analgesics and Narcotic Antagonists"; Side Effects of Drugs (2000) Annual 23, chpt 8 pp. 96-113.

Glatt, William, M.D. FACP, "A New Method for Detoxifying Opoiod-Dependent Patients"; J. Substance Abuse Treatment (1999) vol. 17, No. 3,pp. 193-197.

Gold, et al. "Rapid Opioid Detoxification During General Anesthesia"; Anesthesiology (1999) vol. 91, No. 6, pp. 1639-1647.

Greenwald, et al., "Comparative Clinical Pharmacology of Short-Acting μυ Opioids in Drug Abusers"; J. Pharm and Exper Thera (1996) vol. 277, No. 3, pp. 1228-1236.

Gupta, et al., :Morphine Combined with Doxapram or Naloxone; Anesthesia (1974) vol. 29, pp. 33-39.

Richter et al., "Clinical Investigation on the Development of Dependence during Oral Therapy with Tramadol"; Arzniem-Forsch/Drug Res. 35 (No. II)(1985)pp. 1742-1744.

Rosen et al., "The effect of Lamotrigine on Naloxone-precipitated Opiate withdrawal"; Drug and Alcohol Dependence (1998) vol. 52, pp. 173-176.

Rosen et al., "A Pilot Study of Dextromethorphan in Naloxone-Precipitated Opiate Withdrawal"; European J. of Pharm. (1996) vol. 307, pp. 251-257.

Schuh et al., "Buprenorphine, Morphine and Naloxone Effects during Ascending Morphine Maintenance in Humans"; J. Pharm and Exper Thera (1996) vol. 278, 2, pp. 836-846.

Schuh et al., "Onset, Magnitude and Duration of Opioid Blockade Produced by Buprenorphine and Naltrexone in Humans"; Psychopharmacology (1999) vol. 145, pp. 162-174.

Stevens et al., Nonspecific Excitatory Effects of Morphine: Reverse-Order Precipitated Withdrawal and Dose-Dose Interactions': Psychopharmacology (1981) vol. 75, pp. 210-211.

Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.

Stine et al., "Use of Drug Combinations in Treatment of Opiopd Withdrawal"; J. Clinical Psych. (1992) vol. 12, No. 3, pp. 203-209.

Stoller et al., "Effects of buprenorphine/naloxone in opioid-dependent humans" Psychopharmacology (2001) vol. 154, pp. 230-242.

Strain et al., "Acute Effects of Buprenorphine, hydromorphone and naloxone in methadone-maintained volunteers"; J. Pharm and Exper Thera (1992) vol. 261, No. 3, pp. 985-993.

Strain et al., "Effects of buprenorphine versus buprenorphine/naloxone tablets in non-dependent opioid abusers"; Psychopharmacology (2000) vol. 148, pp. 374-383.

Strain et al., "Precipitated Withdrawal by Pentazocine in Methadone-Maintained Volunteers"; J. Pharm and Exper Thera (1993) vol. 267, No. 2, pp. 624-634.

Tai, et al., "Naltrexone: An Antagonist Therapy for Heroin Addiction"; NIDA (1997) 5 pages.

Umbricht et al., "Naltrexone shortened opioid detoxification with buprenorphine"; Drug and Alcohol Dependence (1999) vol. 56 pp. 181-190.

Vaccarino et al., "Enogenous Opiates: 1999"; Peptides 21 (2000) pp. 1975-2034.

Wang et al., "Inverse Agonists and neutral antagonists at μ opioid receptor (MOR): possible role of basal receptor signaling in narcotic dependence"; J. Neurochemistry (2001) vol. 77, pp. 1590-1600.

Weinberg et al., "Sublingual absorption of selected opioid analgesics"; Clin Pharm Thera (1988) vol. 44, No. 3, pp. 335-342.

Wells, et al., "In vivo Pharmacological Characterization of SoRI 9409, a Nonpeptidic Opioid μ-Agonist/δ-Antagonist that Produces Limited Antinociceptive Tolerance and Attenuates Morphione Physical Dependence"; J. Pharm and Exper Thera (2001) vol. 297, No. 2, pp. 597-605.

Wodak, Alex, "Drug Treatment for Opioid Dependence"; Australian Prescriber (2001) vol. 24, No. 1, pp. 4-6.

Wright et al., "Acute physical dependence in Humans; repeated naloxone-precipitated withdrawal after a single-dose of methadone"; Drug and Alcohol Dependence (1991) vol. 27, pp. 139-148.

Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.

Han et al., "Muccoadhesive buccal disks for novel nalbuphine prodrug controlled delivery; effect of formulation variable on drug release and mucoadhesive performance"; International J. Pharm (1999) vol. 177, pp. 201-209.

Handal et al., "Naloxone"; Annals of Emergency Medicine (1983) vol. 12:7, pp. 438-445.

Harris et al., "Buprenorphine and Naloxone co-administration in opiate dependent patients stabilized on sublingual buprenorphine"; Drug and Alcohol Dependence (2000) vol. 61, pp. 85-94.

Hawkes et al., "Effect of enteric-release formulation of naloxone on intestinal transit in volunteers taking codeine"; Aliment Pharm Ther (2001) vol. 15, pp. 625-630.

Högger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.

Budd, Keith, "Clinical Use of Opioid Antagonists"; Bailliere's Clinical Anesthesiology (1987) vol. 1, No. 4, pp. 993-1011.

Howes et al., "The Pharmacology of TR5109, a new Narcotic Agonist/Antagonist Analgesic"; NIDA Research (1979) pp. 99-105.

Leeling et al., "Disposition and metaboliam of codorphone in the rat, dog, and man"; Drug Metabolism and Disposition (1982) vol. 10, No. 6, pp. 649-653.

Amass et al., "Efficacy of daily and alternate-day dosing regimens with the combibation buprenorphine-naloxone tablet"; Drug and Alcohol Dependence (2000) vol. 58, pp. 143-152.

Hassain et al., "Buccal and oral bioavailability of naloxone and naltrexone in rats";(1987) vol. 36, pp. 127-130.

Jasinski et al., "The human pharmacology and abuse potential of N-allylnoroxymorphone naloxone"; J. Pharm and Exper Thera (1967) vol. 157, No. 2, pp. 420-426.

Jones et al., Nalmefene:blockade of intravenous morphine challenge effects in opioid abusinh humans; Drug and Alcohol Dependence (2000) vol. 60, pp. 29-37.

Kanof et al., "Clinical Charateristics of Naloxone-Precipitated Withdrawal in Human Opioid-Dependent Subjects"; J Pharma and Exper Thera (19920 vol. 260, No. 1, pp. 355-363.

King et al, Naltrexone Biotransformation and Incidence of Subjective Side Effects: A Preliminary Study; Alcoholism: Clin and Exper Res (1997) vol. 21, No. 5, pp. 906-909.

Kogan et al., "Estimation of the Systemic Availability and Other Pharmacokinetic Parameters of Naltrexone in Man after Acute and Chronic Oral Administration"; Res. Comm. In Chem. Path. And Pharm (1977) vol. 18, No. 1, pp. 29-34.

Kosten, Thomas R., M.D.,"Buprenorphine for Benzodiazepine-Abusing Heroin Addicts"; Amer J of Phsychiatry (1994) vol. 1, p. 151.

Kosten et al., "Opioid antagonist challenges in buprenorphine maintained patients"; Drug and Alcohol Dependence (1990) vol. 25, OO. 73-78.

Kurland et al., "Naloxone and the Narcotic Abuser: A Controlled Study of Partial Blockade"; Inter. J. of the Addictions (1974) vol. 9, No. 5, pp. 663-672.

Lee et al., "Nalbuphine Coadministered with Morphine Prevents Tolerance and Dependence"; Anesth Analg (1997) vol. 84, pp. 810-815.

Lehman, et al.,"Influence of Naloxone on the Postoperative Analgesic and Respiratory effects of Buprenorphine"; Eur. J. Clin Pharm (1988) vol. 34, pp. 343-352.

Levine et al., "Potentiation of Pentazocine Analgesia by Low-dose Naloxone"; J Clin Invest (1988) vol. 82, pp. 1574-1577.

Loimer et al., "Combined Naloxone/Methadone Preparations for Opiate Substitution Therapy"; J. of Substance Abuse Treatment (1991) vol. 8, pp. 157-160.

Martin et al. "Bioavailability Investigation of a New Tilidine/Naloxone Liquid Formulation Compared to a Reference Formulation"; Arzneim-Forsch./Drug Res. (1999) vol. 49, pp. 599-607.

Martin et al., "Demonstration of Tolerance to and Physical Dependence on N-allynormorphine (Nalorphine)";J. Of Pharm and Exper Thera (1965) vol. 150, No. 3. pp. 437-442.

Mendelson et al., "Buprenorphine and naloxone combinations: the effects of three dose ratios in morphine stabilized, opiate-dependent volunteers"; Psychopharmacology (1999) vol. 141, pp. 37-46.

Mendelson et al., "Buprenophine and naloxone Interactions in Methadone Maintenance Patients"; Society of Biological Psychiatry (1997) vol. 41, pp. 1095-1101.

Pitts et al., "Antinociceptive and Response Rate-Altering Effects of *Kappa* Opioid Agonists, Spiradoline, Enadoline and U69,593, Alone and in Combination with Opioid Antagonists in Squirrel Monkeys"; J of Pharm and Exper Them (1994) vol. 271, No. 3, pp. 1501-1508.

Preston et al., "Buprenorphine and Naloxone alone and in combination in Opioid-dependant Humans"; Psychopharmacology (1988), vol. 94, pp. 484-490.

Preston et al., "Differential Naltrexone Antagonism of Hydromorphone and Pentazocine Effects in Human Volunteers"; J of Pharm and Ezper Thera (1993) vol. 264, No. 2 pp. 813-823.

Preston et al., "Effects of Sublingually given naloxone in Opioid -dependant human volunteers"; Drug and Alcohol Dependence (1990) vol. 25, pp. 27-34.

Wikler et al., "N-Allylnormorphine: Effects of single dose and Precipitation of Acute "Abstinence Syndromes" during addiction to morphine, methadone or heroin in man (post addicts)"; N-Allylnormorphine During Narcotic Addiction (1953) pp. 8-20.

Zaks et al., "Naloxone Treatment of Opiate Dependence"; JAMA (1971) vol. 215, No. 13, pp. 2108-2110.

Barton, et al., "Intranasal Administration of Naloxone by Paramdeics";Prehospital Emergency Care (2002) vol. 6, No. 1, pp. 54-58.

Blachly, Paul, H., M.D., "Naloxone in Opiate Addiction"; Current Psychiatric Therapies (1976) pp. 209-213.

Bashaw et al., "Relative bioavailability of controlled-release oral morphine sulfate during naltrexone blockade"; Inter J of Clin Pharm and Thea (1995) vol. 33, No. 9, 524-529.

Jasinski, D.R., "Assessment of the Abuse Poteniality of Morphinelike Drugs (Methods Used in Man)"; Drug Addiction (1977) pp. 197-258.

Johnson et al., "Buprenorphine and Naloxone for Heroin Dependence"; Substance Use Disorders (2000) pp. 519-526.

Strain et al., "Opioid antagonist effects of dezocine in opioid-dependent humans"; Clin Pharm and Thera (1996) vol. 60, No. 2, pp. 206-217.

Preston et al., "Abuse liability and studies of opioid agonist-antagonists in humans"; Drug and Alcohol Dependence (1991) vol. 28, pp. 49-82.

Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.

Benfey, "Function of Myocardial α-Adrenoceptors" ; Life Sciences (1982) vol. 31, pp. 101-112.

Levine et al., "Potentiation of Pentazocine Analgesia by Low-dose Naloxone"; J of Clin Invest. (1988) vol. 82, pp. 1547-1577.

Yoburn et al., Opioid Antagonist-induced Receptor Upregulation: Effects of Concurrent Agonist Administration; Brain Research Bulletin (1994), vol. 33, pp. 237-240.

Bunzow et al., "Molecular Closing and Tissue Distribution of a Putative Member of the Rat Opioid Receptor Gene Family that is not a μ, δ, or κ opioid receptor type"; FEBS letters (1994) pp. 284-288.

Mollereau et al., "ORL 1, a novelmember of the opioid receptor family: Cloning, functional expression and localization"; FEBS letters 341 (1994), pp. 33-38.

Wang, et al.,"cDNA cloning a=of an orphan opiate receptor gene family member and its splice variant"; FEBS letters 348 (1994) pp. 75-79.

Suzuki et al., "Morphine conditioned place preference after chronic treatment with naloxone in the rat"; Research Communications in Substance Abuse (1991) vol. 12., No. 3., pp. 119-131.

Press Release "International Patent Application to Be Published on Abuse-Resistant Pain Reliever Being Developed by Perdue Pharma"; Aug. 8, 2001.

Paronis et al., "Increased Analgesic Potency of Mu Agonists after Continuous Naloxone Infusion in Rats"; J fo Pharm Exper Thera (1991), 259 (2), pp. 582-589.

Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.

Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.

Zhang et al., "Down-Regulation of μ-Opioid Receptors in Rat and Monkey Dorsal Root Ganglion Neurons and Spinal Cord After Peripheral Axotomy"; Neuroscience (1998) vol. 82., pp. 223-240.

Abdulla et al., "Axotomy reduces the effect of analgesic opioids yet increases the effect of nociceptin on dorsal root ganglion neurons"; J of Neuro Sci (1998) vol. 18, pp. 9685-9694.

Di Giannuario et al., Orphanin FQ reduces morphine-induced dopamine release in the nucleus accumbens: a microdialysis study in rats; Neurosci. Lett (1999) vol. 272 pp. 183-186.

Ciccocioppo et al., "Effect of Nociceptin/orphanin FQ on the Rewarding Properties of Morphine"; Eur. J Pharmacol (2000) vol. 404, pp. 153-159.

Physician's Desk Reference (2001) see Revia, pp. 1146-1149 and Oxycontin, pp. 2697-2701.

Translation of German patent application DE 43 25 465 published Feb. 2, 1995.

Translation of claims of DE 297 197 04, Nov. 6, 1997.

Caruso et al., "Methadone and Naloxone in Combination (Naldone®) for the Treatment if Heroin Addicts"; Bristol Laboratories, pp. 1336-1341F, (1973).

Fink et al., "Naloxone in Heroin Dependence"; Clin Pharm and Thera. vol. 9, No. 5;pp. 568-577, (1968).

Way et al., "Responsivity to Naloxone during Morphine Dependence"; Annals New York Academy of Sciences, pp. 252-261, (1976).

Crain et al., Ultra-low concentrations of naloxone selectively antagonize excitatory effects of morphine on sensory neurons, thereby increasing its antinociceptive potency and attenuating tolerance/dependence, (1995).

Nutt et al., "Methadone-naloxone mixture for use in methadone maintenance programs"; Clin Pharm and Ther. vol. 15, No. 2., pp. 156-166, (1973).

Parwatikar et al., "Methadone-naloxone in combination for the Treatment of Heroin Addicts"; Clin. Pharm and Thera, vol. 14, No. 6, pp. 941-948 (1973).

Parwartikar et al., "Naloxone-Methadone Combination for the Treatment of Opiate Dependence"; Missouri Institute of Psychiatry, pp. 1350-1354, (1973).

Bigelow et al., "Abuse Liability and Assessment of Buprenorphine-Naloxone Combinations"; Dept of Psychiatry and Behavioral Sciences, The Johns Hopkins University School of Medicine, pp. 145-149, (1987).

* cited by examiner

Figure 1 - Manufacturing Flow Diagram

Mean Plasma Naloxone Concentration-Time Profiles Following Each Treatment

Spaghetti Plots of Individual Plasma Concentrations of Naloxone

Mean (± SD) Plasma Concentrations of Oxycodone Over Time by Treatment
Population (N = 94)   Subject 21 was dosed with oxycodone controlled-release with naloxone in both periods and was excluded

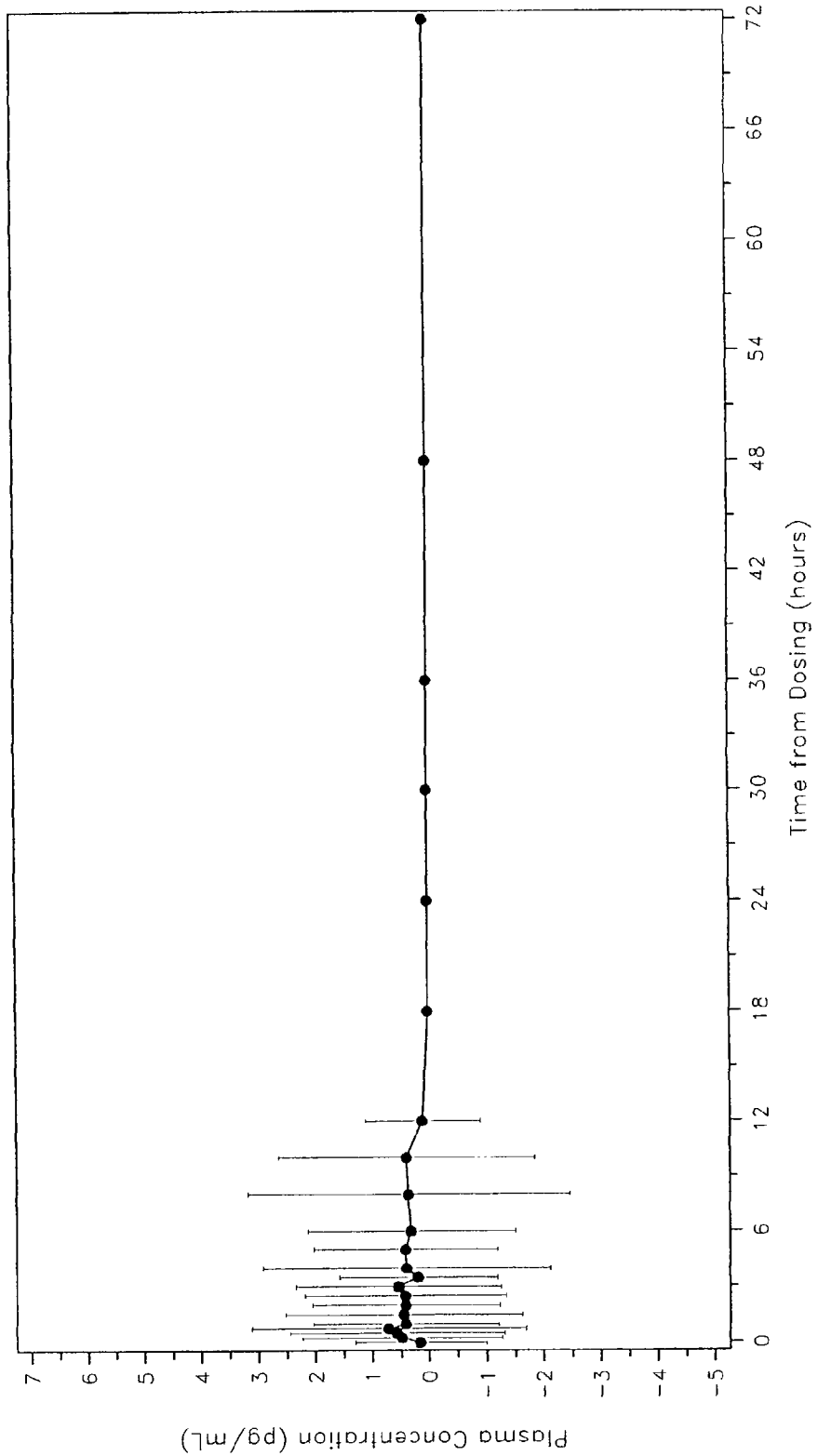

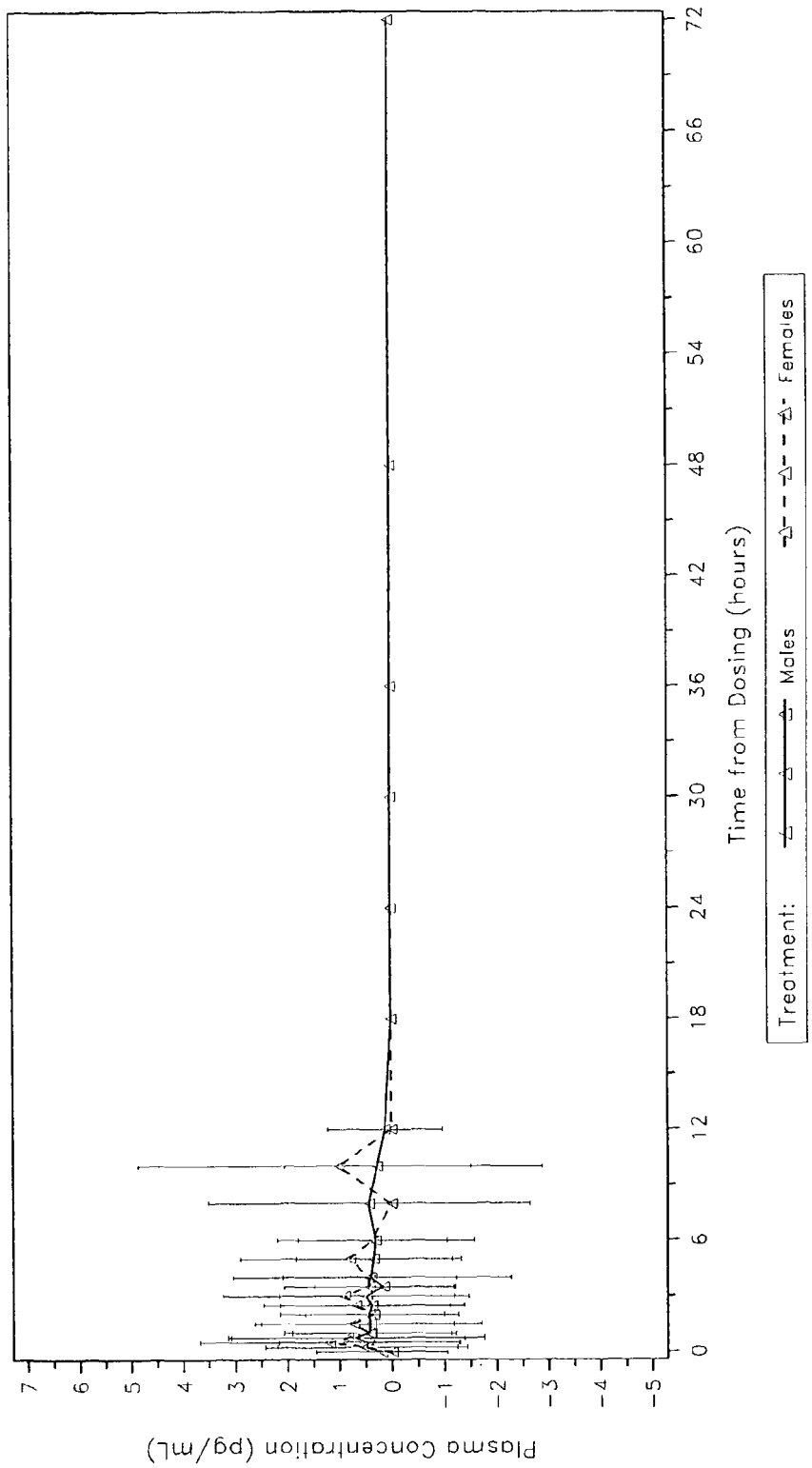

PHARMACEUTICAL COMBINATIONS OF OXYCODONE AND NALOXONE

This application claims the benefit of U.S. Provisional Application No. 60/306,301, filed Jul. 18, 2001, hereby incorporated by reference.

BACKGROUND OF THE INVENTION

Oxycodone formulations are sometimes the subject of abuse. A particular dose of oxycodone may be more potent when administered parenterally as compared to the same dose administered orally. One mode of abuse of oral oxycodone formulations involves putting the active agent in solution and injecting it. Opioid antagonists have been combined with certain opioid agonists in order to deter the parenteral abuse of these drugs.

In the prior art, the combination of immediate release pentazocine and naloxone has been utilized in tablets available in the United States, commercially available as Talwin®Nx from Sanofi-Winthrop. Talwin®Nx contains immediate release pentazocine hydrochloride equivalent to 50 mg base and naloxone hydrochloride equivalent to 0.5 mg base. A fixed combination therapy comprising tilidine (50 mg) and naloxone (4 mg) has been available in Germany for the management of pain since 1978 (Valoron®N, Goedecke). A fixed combination of buprenorphine and naloxone was introduced in 1991 in New Zealand (Temgesic®Nx, Reckitt & Colman) for the treatment of pain.

Purdue Pharma L.P currently has marketed sustained-release oxycodone in dosage forms containing 10, 20, 40, 80 and 160 mg oxycodone hydrochloride under the tradename OxyContin®.

U.S. Pat. Nos. 5,266,331; 5,508,042; 5,549,912 and 5,656,295 disclose sustained release oxycodone formulations.

U.S. Pat. Nos. 4,769,372 and 4,785,000 to Kreek purport to describe methods of treating patients suffering from chronic pain or chronic cough without provoking intestinal dysmotility by administering 1 to 2 dosage units comprising from about 1.5 to about 100 mg of opioid analgesic or antitussive and from about 1 to about 18 mg of an opioid antagonist having little to no systemic antagonist activity when administered orally, from 1 to 5 times daily.

U.S. Pat. No. 5,472,943 to Crain et al. purports to describe methods of enhancing the analgesic potency of bimodally acting opioid agonists by administering the agonist with an opioid antagonist.

U.S. Pat. No. 3,773,955 purports to describe immediate release formulations comprising opioid agonists in combination with 0.1 to 2.5 mg naloxone.

All documents cited herein, including the foregoing are incorporated by reference in their entireties for all purposes.

OBJECTS AND SUMMARY OF THE INVENTION

It is an object of the invention to provide an oral dosage form comprising oxycodone or a salt thereof.

It is an object of certain embodiments of the invention to provide an oral dosage form of oxycodone or salt thereof which is subject to less parenteral abuse than other dosage forms.

It is an object of certain embodiments of the invention to provide an oral dosage form of oxycodone or salt thereof which is less attractive to addicts than other dosage forms.

It is an object of certain embodiments of the invention to provide an oral dosage form of oxycodone or salt thereof which is subject to less diversion than other dosage forms.

It is an object of certain embodiments of the invention to provide a method of treating pain in human patients with an oral dosage form of oxycodone or salt thereof while reducing the abuse potential of the dosage form.

It is an object of certain embodiments of the invention to provide a method of manufacturing an oral dosage form of oxycodone or salt thereof such that it has less abuse potential.

These objects and others are achieved by the present invention, which is directed to a pharmaceutical composition comprising from 10 to 40 mg of oxycodone or a pharmaceutically acceptable salt thereof and 0.65 to 0.90 mg naloxone or a pharmaceutically acceptable salt thereof.

In certain embodiments, the invention is directed to a pharmaceutical composition comprising about 10 mg oxycodone hydrochloride and 0.80 to 0.90 mg naloxone hydrochloride in a dosage form that provides sustained release of at least the oxycodone hydrochloride.

In certain embodiments, the invention is directed to a pharmaceutical composition comprising about 20 mg oxycodone hydrochloride and 0.80 to 0.90 mg naloxone hydrochloride in a dosage form that provides sustained release of at least the oxycodone hydrochloride.

In certain embodiments, the invention is directed to a pharmaceutical composition comprising about 40 mg oxycodone hydrochloride and 0.80 to 0.90 mg naloxone hydrochloride in a dosage form that provides sustained release of at least the oxycodone hydrochloride.

In certain embodiments, the invention is directed to a pharmaceutical composition comprising about 10 mg oxycodone hydrochloride and 0.80 to 0.90 mg naloxone hydrochloride dihydrate in a dosage form that provides sustained release of at least the oxycodone hydrochloride.

In certain embodiments, the invention is directed to a pharmaceutical composition comprising about 20 mg oxycodone hydrochloride and 0.80 to 0.90 mg naloxone hydrochloride dihydrate in a dosage form that provides sustained release of at least the oxycodone hydrochloride.

In certain embodiments, the invention is directed to a pharmaceutical composition comprising about 40 mg oxycodone hydrochloride and 0.80 to 0.90 mg naloxone hydrochloride dihydrate in a dosage form that provides sustained release of at least the oxycodone hydrochloride.

In certain embodiments of the invention disclosed herein, the dosage form provides sustained release of the naloxone or pharmaceutically acceptable salt thereof.

In certain embodiments which provide sustained release of the oxycodone or salt thereof and the naloxone or salt thereof, the dosage form when tested in-vitro by the USP Apparatus I (Basket) method of U.S. Pharmacopeia XXIV (2000) at 100 rpm in 900 ml simulated gastric fluid (SGF) at 37° C. provides a dissolution of the naloxone or pharmaceutically acceptable salt thereof which is within ±30% relative to the dissolution rate of the oxycodone or pharmaceutically acceptable salt thereof at 1 hour, 4 hours and 12 hours. For example, if the dissolution rate of the oxycodone or pharmaceutically acceptable salt thereof is 40% at 1 hour, the dissolution rate of the naloxone or pharmaceutically acceptable salt thereof would be from 28% to 52%.

In certain of the above embodiments, the naloxone or pharmaceutically acceptable salt thereof has an in-vitro dissolution rate at the 1 hour, 4 hour and 12 hour time points within ±20% relative to the dissolution rate of the oxycodone or pharmaceutically acceptable salt thereof; alternatively within ±10% relative to the dissolution rate of the oxycodone or pharmaceutically acceptable salt thereof; or alternatively within ±5% relative to the dissolution rate of the oxycodone or pharmaceutically acceptable salt thereof.

In other embodiments which provide sustained release of the oxycodone or salt thereof and the naloxone or salt thereof, the in-vitro dissolution rate of the oxycodone or pharmaceutically acceptable salt thereof and naloxone or pharmaceutically acceptable salt thereof when measured by the USP Apparatus I (Basket) method of U.S. Pharmacopeia XXIV (2000) at 100 rpm in 900 ml simulated gastric fluid (SGF) at 37° C. is from about 20 to about 60% (by weight) oxycodone or pharmaceutically acceptable salt thereof and from about 20 to about 60% (by weight) naloxone or pharmaceutically acceptable salt thereof released at 1 hour; from about 30 to about 75% (by weight) oxycodone or pharmaceutically acceptable salt thereof and from about 30% to about 75% (by weight) naloxone or pharmaceutically acceptable salt thereof released at 2 hours; from about 40 to about 90% (by weight) oxycodone or pharmaceutically acceptable salt thereof and from about 40 to about 90% (by weight) naloxone or pharmaceutically acceptable salt thereof released at 4 hours; greater than about 60% (by weight) oxycodone or pharmaceutically acceptable salt thereof and greater than about 60% (by weight) naloxone or pharmaceutically acceptable salt thereof released at 8 hours; and greater than about 70% (by weight) oxycodone or pharmaceutically acceptable salt thereof and greater than about 70% (by weight) naloxone or pharmaceutically acceptable salt thereof released at 12 hours.

In other embodiments which provide sustained release of the oxycodone or salt thereof and the naloxone or salt thereof, the in-vitro dissolution rate of the oxycodone or pharmaceutically acceptable salt thereof and naloxone or pharmaceutically acceptable salt thereof when measured by the USP Apparatus I (Basket) method of U.S. Pharmacopeia XXIV (2000) at 100 rpm in 900 ml simulated gastric fluid (SGF) at 37° C. is from about 30 to 60% (by weight) oxycodone or pharmaceutically acceptable salt thereof and from about 30 to about 60% (by weight) naloxone or pharmaceutically acceptable salt thereof released at 1 hour; from about 40 to about 70% (by weight) oxycodone or pharmaceutically acceptable salt thereof and from about 40% to about 70% (by weight) naloxone or pharmaceutically acceptable salt thereof released at 2 hours; from about 55 to about 90% (by weight) oxycodone or pharmaceutically acceptable salt thereof and from about 55 to about 90% (by weight) naloxone or pharmaceutically acceptable salt thereof released at 4 hours; greater than about 70% (by weight) oxycodone or pharmaceutically acceptable salt thereof and greater than about 70% (by weight) naloxone or pharmaceutically acceptable salt thereof released at 8 hours; and greater than about 80% (by weight) oxycodone or pharmaceutically acceptable salt thereof and greater than about 80% (by weight) naloxone or pharmaceutically acceptable salt thereof released at 12 hours.

In certain embodiments, the pharmaceutical composition of the present invention provides a mean AUC of plasma oxycodone within 80% to 125% of the mean AUC of plasma oxycodone provided by an oxycodone base equivalent amount of a controlled release reference product (OxyContin® as described in the Physician's Desk Reference 2002) upon single dose administration to a population of human subjects. In other embodiments, the mean AUC of plasma oxycodone is within 90% to 110%, or 95% to 105% of the mean AUC of plasma oxycodone provided by an oxycodone base equivalent amount of the controlled release reference product upon single dose administration to a population of human subjects.

In certain embodiments, the pharmaceutical composition of the present invention provides a mean Cmax of plasma naloxone which is at least 50% less than the mean Cmax of plasma naloxone provided by a naloxone base equivalent amount of an immediate release reference product containing naloxone hydrochloride, i.e., Talwin® Nx as described in the Physician's Desk Reference 2002. In other embodiments, the mean Cmax of plasma naloxone is at least 65% less than, or at least 80% less than the mean Cmax of plasma naloxone provided by a naloxone base equivalent amount of the immediate release reference product containing naloxone hydrochloride, i.e., Talwin® Nx as described in the Physician's Desk Reference 2002.

In certain embodiments, the pharmaceutical composition of the present invention provides a mean Cmax of plasma naloxone of less than 180 pg/ml, less than 150 pg/ml or less than 100 pg/ml upon single dose administration to a population of human subjects. In more preferred embodiments, the mean Cmax of plasma naloxone is less than 50 pg/ml, less than 10 pg/ml or less than 5 pg/ml upon single dose administration to a population of human subjects.

In certain embodiments, the pharmaceutical composition of the present invention contains any amount of naloxone or a pharmaceutically acceptable salt thereof to provide a mean Cmax of plasma naloxone of less than 5 pg/ml upon single dose administration to a population of human subjects.

In certain embodiments of the invention disclosed herein, the dosage form provides effective pain relief for at least 12 hours after steady state oral administration to human patients.

In certain embodiments of the invention disclosed herein, the dosage form provides effective pain relief for at least 24 hours after steady state oral administration to human patients.

In certain embodiments of the invention disclosed herein, the dosage form comprises a matrix comprising the oxycodone hydrochloride and the naloxone hydrochloride interdispersed in a sustained release excipient.

In certain embodiments, the invention is directed to a method of reducing the potential of parenteral abuse of an oxycodone formulation comprising preparing the compositions disclosed herein.

In certain embodiments, the invention is directed to a method of treating pain in a human patient comprising orally administering a sustained release oral dosage form as described herein.

In certain embodiments, the invention is directed to a method of treating pain in a human patient comprising orally administering a sustained release oral dosage form as described every 12 hours at least until steady state is achieved.

In certain embodiments, the invention is directed to a method of treating pain in a human patient comprising orally administering a sustained release oral dosage form as described every 24 hours at least until steady state is achieved.

In certain embodiments, the invention is directed to a method of treating pain in a human patient comprising orally administering a pharmaceutical composition as disclosed herein that provides effective pain relief for at least 12 hours after steady state oral administration to the patient.

In certain embodiments, the invention is directed to a method of treating pain in a human patient comprising orally administering a pharmaceutical composition as disclosed herein that provides effective pain relief for at least 24 hours after steady state oral administration to the patient.

In certain embodiments, the invention is directed to a method of manufacturing a sustained release oral dosage form comprising combining oxycodone or a pharmaceutically acceptable salt thereof with a sustained release excipient to form a oxycodone/excipient combination; adding naloxone or a pharmaceutically acceptable salt thereof to the oxycodone/excipient combination; and forming a sustained release oral dosage form of oxycodone or a pharmaceutically acceptable salt thereof and naloxone or a pharmaceutically acceptable salt thereof. Alternatively, the naloxone can be combined first with excipient, with the oxycodone added to the naloxone/excipient mixture. In other embodiments, the oxycodone and the naloxone can be combined concurrently or before combination with the excipient. In certain embodiments, one agent is not pretreated to be in sustained release form prior to combination with the other agent.

In certain embodiments, the invention is directed to a method of treating pain comprising administering a pharmaceutical composition comprising an amount of oxycodone or pharmaceutically acceptable salt thereof equivalent to about 10 mg oxycodone hydrochloride and 0.65 to 0.90 mg naloxone or pharmaceutically acceptable salt thereof in a dosage form that provides sustained release of at least the oxycodone hydrochloride and thereafter increasing the dosage by administering a pharmaceutical composition comprising an amount of oxycodone or pharmaceutically acceptable salt thereof equivalent to about 20 mg oxycodone hydrochloride and 0.65 to 0.90 mg naloxone or pharmaceutically acceptable salt thereof in a dosage form that provides sustained release of at least the oxycodone hydrochloride.

In certain embodiments, the invention is directed to a method of treating pain comprising administering a pharmaceutical composition comprising an amount of oxycodone or pharmaceutically acceptable salt thereof equivalent to about 20 mg oxycodone hydrochloride and 0.65 to 0.90 mg naloxone or pharmaceutically acceptable salt thereof in a dosage form that provides sustained release of at least the oxycodone hydrochloride and thereafter increasing the dosage by administering a pharmaceutical composition comprising an amount of oxycodone or pharmaceutically acceptable salt thereof equivalent to about 40 mg oxycodone hydrochloride and 0.65 to 0.90 mg naloxone or pharmaceutically acceptable salt thereof in a dosage form that provides sustained release of at least the oxycodone hydrochloride.

In certain embodiments, the invention is directed to a method of treating pain comprising administering a pharmaceutical composition comprising an amount of oxycodone or pharmaceutically acceptable salt thereof equivalent to about 10 mg oxycodone hydrochloride and 0.65 to 0.90 mg naloxone or pharmaceutically acceptable salt thereof in a dosage form that provides sustained release of at least the oxycodone hydrochloride and thereafter increasing the dosage by administering a pharmaceutical composition comprising an amount of oxycodone or pharmaceutically acceptable salt thereof equivalent to about 20 mg oxycodone hydrochloride and 0.65 to 0.90 mg naloxone or pharmaceutically acceptable salt thereof in a dosage form that provides sustained release of at least the oxycodone hydrochloride and thereafter increasing the dosage by administering a pharmaceutical composition comprising an amount of oxycodone or pharmaceutically acceptable salt thereof equivalent to about 40 mg oxycodone hydrochloride and 0.65 to 0.90 mg naloxone or pharmaceutically acceptable salt thereof in a dosage form that provides sustained release of at least the oxycodone hydrochloride.

In certain embodiments, the invention is directed to a kit for the treatment of pain comprising a container comprising at least one formulation comprising about 10 to about 40 mg oxycodone or a pharmaceutically acceptable salt thereof and naloxone or a pharmaceutically acceptable salt thereof; the kit further comprising indicia indicating the use of the formulation. In certain embodiments, the formulation of the kit comprises from 0.65 to 0.9 mg naloxone or a pharmaceutically acceptable salt thereof and in certain embodiments the indicia indicates that the use is to reduce the parenteral abuse of the formulation.

The term "sustained release" is defined for purposes of the present invention as the release of the oxycodone or salt thereof to maintain blood (e.g., plasma) concentrations within the therapeutic range but below toxic levels over an extended period of time as compared to an immediate release product, e.g., from about 12 to about 24 hours. Preferably the sustained release is sufficient to provide a twice-a-day or a once-a-day formulation. In certain embodiments, the release rate of the naloxone or salt thereof is within ±30% relative to the dissolution rate of the oxycodone or pharmaceutically acceptable salt thereof at 1 hour, 4 hours and 12 hours.

The term "parenterally" as used herein includes subcutaneous injections, intravenous, intramuscular, intrasternal injection, infusion techniques or other methods of injection known in the art.

Unless otherwise noted, the term "oxycodone" means oxycodone base. Unless otherwise noted, the term "naloxone" means naloxone base. The term salt means a pharmaceutically acceptable salt.

The term "steady state" means that the amount of the drug reaching the system is approximately the same as the amount of the drug leaving the system. Thus at "steady state", the patient's body eliminates the drug at approximately the same rate that the drug becomes available to the patient's system through absorption into the blood stream.

The term "parenterally effective amount of naloxone or pharmaceutically acceptable salt thereof" means that the naloxone or pharmaceutically acceptable salt thereof is in an amount that is sufficient to antagonize or partially antagonize the effect of the oxycodone upon parenteral administration of the dosage form and below an amount that antagonizes or partially antagonizes the effect of the oxycodone upon oral administration of the dosage form.

The term "mean" unless otherwise specified refers to the arithmetic mean.

The term "human subject" means a healthy human subject with normal metabolism as understood by one skilled in the art.

BRIEF DESCRIPTION OF THE DRAWINGS

FIG. 5 is a graphical representation of the mean observed plasma concentration over time for naloxone for all subjects evaluable for safety.

FIG. 6 is a graphical representation of the mean observed plasma concentration over time by gender for naloxone for all subjects evaluable for safety.

DETAILED DESCRIPTION OF THE INVENTION

Figure 1:
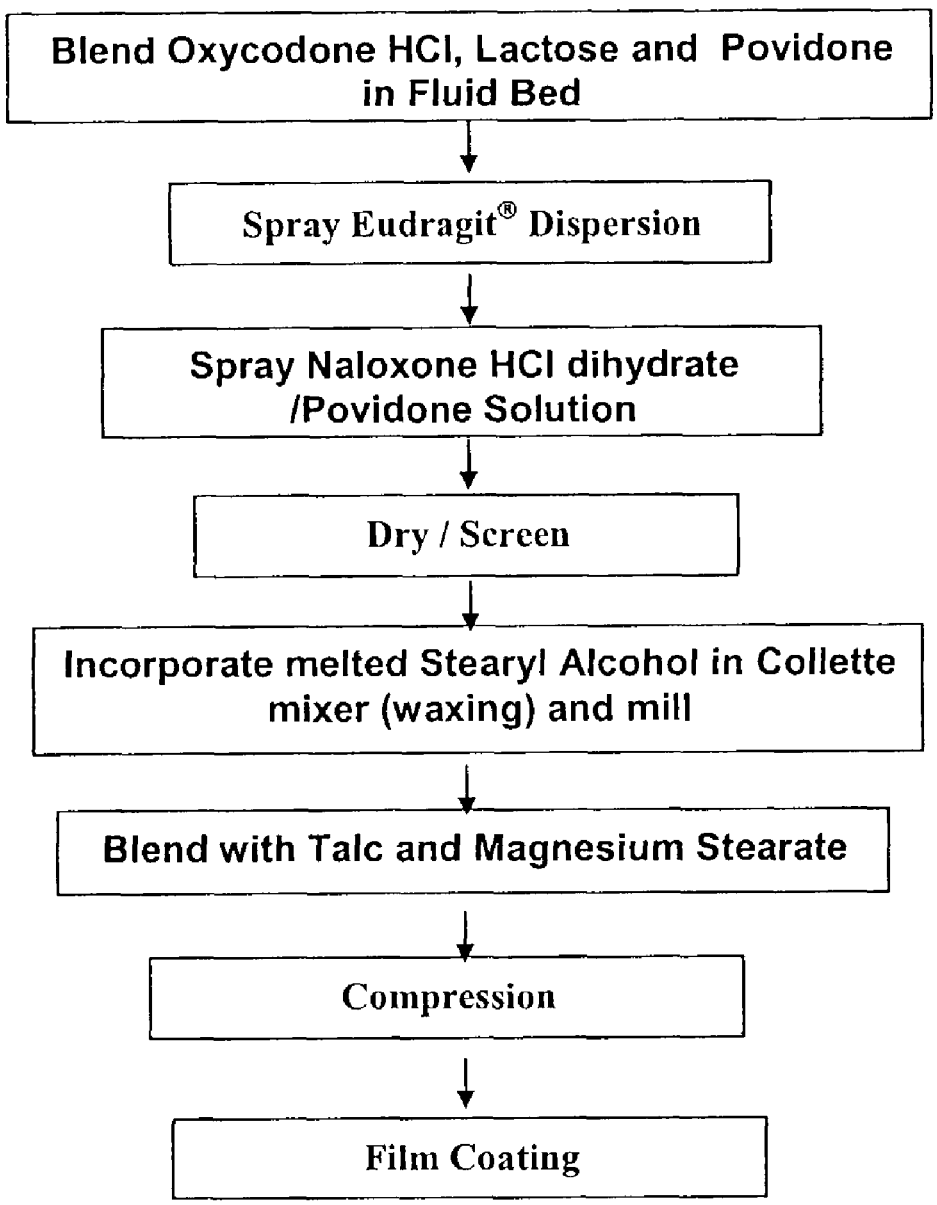
FIG. 1 is a flow diagram of a method of producing an embodiment of the present invention.
Figure 2:
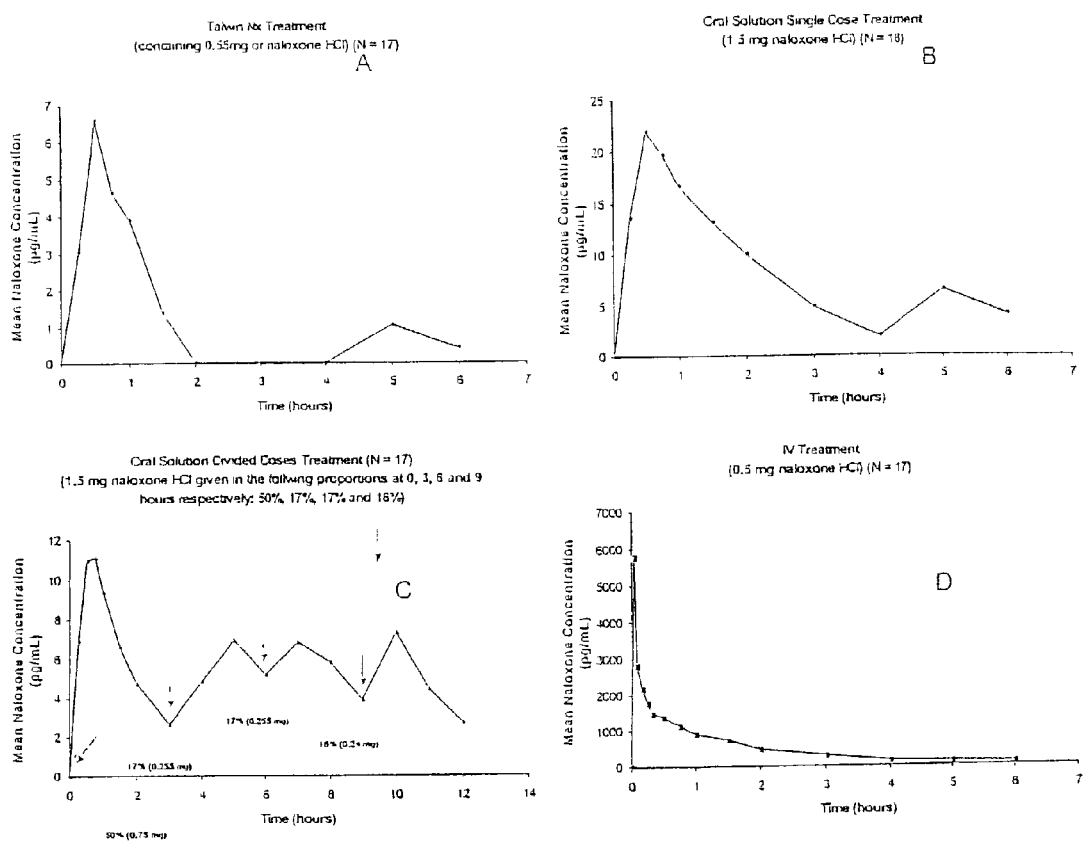
FIGS. 2A, 2B, 2C, and 2D are graphical representations of the mean of the observed plasma concentration-time profiles for naloxone for the four treatment arms of Example 8.
Figure 3:
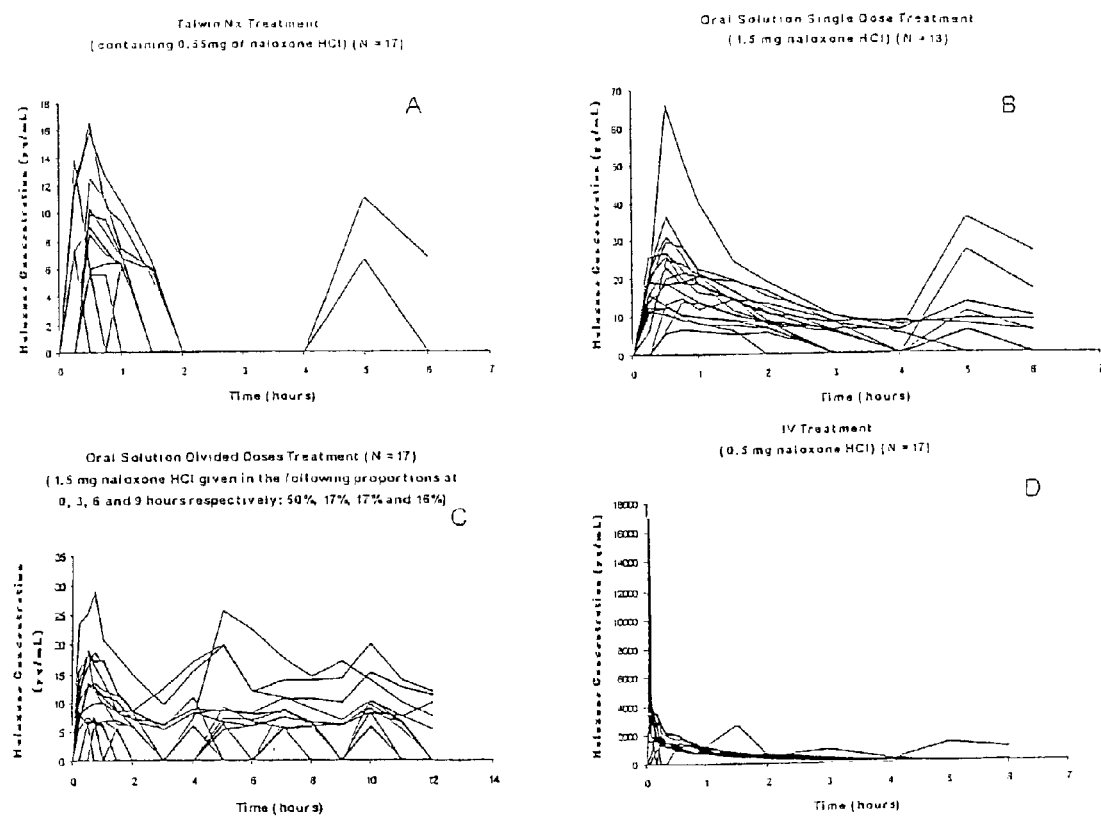
FIGS. 3A, 3B, 3C and 3D are graphical representations of the observed individual plasma concentration-time profiles for naloxone for the four treatment arms.

The dosage form of the present invention contains an amount of oxycodone or pharmaceutically acceptable salts thereof equivalent to about 10 to about 40 mg of oxycodone hydrochloride. Particularly preferred dosages of oxycodone hydrochloride are about 10 mg, about 20 mg, about 30 mg or about 40 mg. The oxycodone or salt thereof is formulated with suitable pharmaceutically acceptable excipients to provide a sustained release of the oxycodone.

The dosage form of the present invention contains about 0.65 to about 0.90 mg of naloxone or pharmaceutically acceptable salts thereof. Particularly preferred dosage ranges of naloxone salt are about 0.82 to about 0.88 mg, and about 0.84 to about 0.86 mg. Particularly preferred dosages have about 0.85 mg of naloxone salt. Particularly preferred dosage ranges of naloxone base are about 0.65 to about 0.75 mg, and about 0.67 to about 0.73 mg. Particularly preferred dosages have about 0.70 mg of naloxone base.

The dosage form of the present invention contains an amount of naloxone or pharmaceutically acceptable salts thereof equivalent to about 0.65 to about 0.90 mg of naloxone hydrochloride dihydrate. Particularly preferred dosage ranges of naloxone hydrochloride dihydrate are about 0.82 to about 0.88 mg, or about 0.84 to about 0.86 mg. Particularly preferred dosages have about 0.85 mg of naloxone hydrochloride dihydrate. Particularly preferred dosage ranges of naloxone base are about 0.65 to about 0.75 mg, or an equivalent amount of a salt thereof and about 0.67 to about 0.73 mg or an equivalent amount of a salt thereof. Particularly preferred dosages have about 0.70 mg of naloxone base or an equivalent amount of a salt thereof.

The naloxone or salt thereof can be formulated to provide immediate release or can be combined with suitable pharmaceutically acceptable excipients to provide a sustained release of the naloxone or salt thereof. The rate of sustained release of the naloxone or salt thereof can be the same or different than the rate of sustained release of the oxycodone or salt thereof. Particularly preferred embodiments of the present invention are dosage forms which comprise 10 mg oxycodone hydrochloride and 0.85 mg naloxone hydrochloride; 20 mg oxycodone hydrochloride and 0.85 mg naloxone hydrochloride; 30 mg oxycodone hydrochloride and 0.85 mg naloxone hydrochloride; 40 mg oxycodone hydrochloride and 0.85 mg naloxone hydrochloride; or equivalent amounts of oxycodone base, naloxone base or other pharmaceutically acceptable salts thereof. Hydrochloride salts of oxycodone and naloxone are particularly preferred.

Other particularly preferred embodiments of the present invention are dosage forms which comprise 10 mg oxycodone hydrochloride and 0.85 mg naloxone hydrochloride dihydrate; 20 mg oxycodone hydrochloride and 0.85 mg naloxone hydrochloride dihydrate; 30 mg oxycodone hydrochloride and 0.85 mg naloxone hydrochloride dihydrate; or 40 mg oxycodone hydrochloride and 0.85 mg naloxone hydrochloride dihydrate.

In embodiments wherein the agents are both in sustained release, the dosage form preferably releases the oxycodone or pharmaceutically acceptable salt thereof and the naloxone or pharmaceutically acceptable salt thereof to provide in-vitro dissolution rates when measured by the USP Apparatus I (Basket) method of U.S. Pharmacopeia XXIV (2000) at 100 rpm in 900 ml simulated gastric fluid (SGF) at 37° C. in accordance with the objects of the invention.

The disclosed range of naloxone or salt thereof in the present invention is a parenterally effective amount to deter intravenous abuse by at least partially blocking the opioid effects of oxycodone if the formulation is dissolved and parenterally administered. Preferably the amount is also sufficient upon parenteral administration in most physically dependent individuals, to precipitate a moderate to severe withdrawal syndrome that is very similar to that seen after abrupt withdrawal of opioids. The most common symptoms of the withdrawal syndrome include anorexia, weight loss, pupillary dilation, chills alternating with excessive sweating, abdominal cramps, nausea, vomiting, muscle spasms, hyper-irritability, lachrymation, rinorrhea, goose flesh and increased heart rate. The amount of naloxone should not cause an adverse effect or a reduction in analgesic efficacy upon oral administration to a patient in pain.

Sustained Release Dosage Forms

The oxycodone (or oxycodone salt) and optionally the naloxone (or naloxone salt) is formulated as a sustained release oral formulation in any suitable tablet, coated tablet or multiparticulate formulation known to those skilled in the art. The sustained release dosage form may include a sustained release material which is incorporated into a matrix along with the oxycodone or salt thereof with or without the naloxone or salt thereof. For example, oxycodone salt can be incorporated in a sustained release matrix and naloxone salt can be separate from the matrix or can be incorporated into the matrix.

The sustained release dosage form may optionally comprise particles containing oxycodone or salt thereof with or without the naloxone or salt thereof. In certain embodiments, the particles have a diameter from about 0.1 mm to about 2.5 mm, preferably from about 0.5 mm to about 2 mm. The naloxone or naloxone salt may be incorporated into particles which contain oxycodone or oxycodone salt, or may be incorporated into a tablet or capsule containing oxycodone or oxycodone salt particles. Preferably, the particles are film coated with a material that permits release of the active(s) at a sustained rate in an aqueous medium. The film coat is chosen so as to achieve, in combination with the other stated properties, a desired in-vitro release rate. The sustained release coating formulations of the present invention should be capable of producing a strong, continuous film that is smooth and elegant, capable of supporting pigments and other coating additives, non-toxic, inert, and tack-free.

Coated Beads

In certain embodiments of the present invention a hydrophobic material is used to coat inert pharmaceutical beads such as nu pariel 18/20 beads, and a plurality of the resultant solid sustained release beads may thereafter be placed in a gelatin capsule in an amount sufficient to provide an effective sustained release dose when ingested and contacted by an environmental fluid, e.g., gastric fluid or dissolution media. In certain embodiments the naloxone or naloxone salt may be coated onto a sustained release bead containing oxycodone or oxycodone salt, or may be placed in a capsule with the sustained release oxycodone or oxycodone salt beads.

The sustained release bead formulations of the present invention slowly release the agent(s) of the present invention, e.g., when ingested and exposed to gastric fluids, and then to intestinal fluids. The sustained release profile of the formulations of the invention can be altered, for example, by varying the amount of overcoating with the hydrophobic material, altering the manner in which a plasticizer is added to the hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with the agent(s) of the present are prepared, e.g., by dissolving the agent(s) in water and then spraying the solution onto a substrate, for example, nu pariel 18/20 beads, using a Wuster insert. Optionally, additional ingredients are also added prior to coating the beads in order to assist the binding of the agent(s) to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the active(s) from the hydrophobic sustained release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

Plasticized hydrophobic material may be applied onto the substrate comprising the agent(s) by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the hydrophobic material to obtain a predetermined sustained release of the agent(s) when the coated substrate is exposed to aqueous solutions, e.g. gastric fluid, may be applied. After coating with the hydrophobic material, a further overcoat of a film-former, such as Opadry®, is optionally applied to the beads. This overcoat is provided, if at all, in order to substantially reduce agglomeration of the beads.

The release of the agent(s) from the sustained release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in an environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,899; 4,063,064; and 4,088,864. The passageway can have any shape such as round, triangular, square, elliptical, irregular, etc.

Matrix Formulations

In other embodiments of the present invention, the sustained release formulation is achieved via a matrix optionally having a sustained release coating as set forth herein. The materials suitable for inclusion in a sustained release matrix may depend on the method used to form the matrix.

For example, a matrix in addition to the oxycodone (or oxycodone salt) and optional naloxone (or naloxone salt) may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting sustained release of the agent(s) and which melts (or softens to the extent necessary to be extruded) may be used in accordance with the present invention.

Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

Of these polymers, acrylic polymers, especially Eudragit® RSPO—the cellulose ethers, especially hydroxyalkylcelluloses and carboxyalkylcelluloses, are preferred. The oral dosage form may contain between 1% and 80% (by weight) of at least one hydrophilic or hydrophobic material.

When the hydrophobic material is a hydrocarbon, the hydrocarbon preferably has a melting point of between 25° and 90° C. Of the long chain hydrocarbon materials, fatty (aliphatic) alcohols are preferred. The oral dosage form may contain up to 60% (by weight) of at least one digestible, long chain hydrocarbon.

Preferably, the oral dosage form contains up to 60% (by weight) of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 25° to about 200° C., preferably from about 45° C. to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 25° to about 100° C.

Suitable hydrophobic materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon.

Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of oxycodone release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of oxycodone release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a (w/w) of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable sustained release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a sustained release matrix may also contain suitable quantities of other materials, e.g. diluents, lubricants, binders, granulating aids, colorants, flavorants and glidants that are conventional in the pharmaceutical art.

Matrix-Particulates

In order to facilitate the preparation of a solid, sustained release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose, and the oxycodone (or oxycodone salt) and optionally the naloxone (or naloxone salt); (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxalkyl cellulose granules with water.

In yet other alternative embodiments, a spheronizing agent, together with the oxycodone (or oxycodone salt) and optionally the naloxone (or naloxone salt) can be spheronized to form spheroids. Microcrystalline cellulose is a preferred spheronizing agent. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation.

In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the *Handbook of Pharmaceutical Excipients*, American Pharmaceutical Association (1986).

Melt Extrusion Multiparticulates

The preparation of a suitable melt-extruded matrix according to the present invention may, for example, include the steps of blending the oxycodone (or oxycodone salt) and/or the naloxone (or naloxone salt) together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, the oxycodone (or oxycodone salt) and optionally the naloxone (or naloxone salt), and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in *Remington's Pharmaceutical Sciences*, (Arthur Osol, editor), 1553-1593 (1980).

In yet another preferred embodiment, the extrudate can be shaped into tablets as set forth in U.S. Pat. No. 4,957,681 (Klimesch, et. al.), described in additional detail above.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the desired release rate, among other things.

The melt-extruded unit dosage forms of the present invention may further include combinations of melt-extruded particles (e.g., one group of particles with oxycodone (or oxycodone salt) and one group of particles with naloxone (or naloxone salt)) before being encapsulated. Furthermore, the unit dosage forms can also include an amount of an immediate release agent for prompt release. The immediate release agent may be incorporated, e.g., as separate pellets within a gelatin capsule, or may be coated on the surface of the multiparticulates after preparation of the dosage forms (e.g., sustained release coating or matrix-based). The unit dosage forms of the present invention may also contain a combination of sustained release beads and matrix multiparticulates to achieve a desired effect.

The sustained release formulations of the present invention preferably slowly release the agent(s), e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the oxycodone (or oxycodone salt) and the naloxone (or naloxone salt), which can be added thereafter to the extrudate. Such formulations typically will have the agents blended together with the extruded matrix material, and then the mixture would be tableted in order to provide a slow release formulation.

Coatings

The dosage forms of the present invention may optionally be coated with one or more materials suitable for the regulation of release or for the protection of the formulation. In one embodiment, coatings are provided to permit either pH-dependent or pH-independent release. A pH-dependent coating serves to release the oxycodone in desired areas of the gastrointestinal (GI) tract, e.g., the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the oxycodone or salt thereof and optionally the naloxone or salt thereof is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Coatings derived from aqueous dispersions are described, e.g., in detail in U.S. Pat. Nos. 5,273,760 and 5,286,493.

Other examples of sustained release formulations and coatings which may be used in accordance with the present invention include U.S. Pat. Nos. 5,324,351; 5,356,467, and 5,472,712.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use. Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the sustained release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Rohm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH <5.7 and is soluble at about pH >6. Eudragit® S does not swell at about pH <6.5 and is soluble at about pH >7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethyl-cellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Sustained Release Osmotic Dosage Form

Sustained release dosage forms according to the present invention may also be prepared as osmotic dosage formulations. The osmotic dosage forms preferably include a bilayer core comprising a drug layer (containing the oxycodone (or oxycodone salt) and optionally the naloxone (or naloxone salt)) and a delivery or push layer (which may contain the naloxone (or naloxone salt)), wherein the bilayer core is surrounded by a semipermeable wall and optionally having at least one passageway disposed therein.

The expression "passageway" as used for the purpose of this invention, includes aperture, orifice, bore, pore, porous element through which oxycodone or oxycodone salt (with or without the naloxone or naloxone salt) can be pumped, diffuse or migrate through a fiber, capillary tube, porous overlay, porous insert, microporous member, or porous composition. The passageway can also include a compound that erodes or is leached from the wall in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The passageway can have any shape, such as round, triangular, square and elliptical, for assisting in the sustained metered release of oxycodone or oxycodone salt from the dosage form. The dosage form can be manufactured with one or more passageways in spaced-apart relation on one or more surfaces of the dosage form. A passageway and equipment for forming a passageway are disclosed in U.S. Pat. Nos. 3,845,770; 3,916,899; 4,063,064 and 4,088,864. Passageways comprising sustained-release dimensions sized, shaped and adapted as a releasing-pore formed by aqueous leaching to provide a releasing-pore of a sustained-release rate are disclosed in U.S. Pat. Nos. 4,200,098 and 4,285,987.

In certain embodiments, the bilayer core comprises a drug layer with oxycodone or a salt thereof and a displacement or push layer containing the naloxone or a salt thereof. In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_n \cdot H_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxy methylcellulose, sodium carboxyethylcellulose, lithium carboxymethylcellulose, sodium carboxyethylcellulose, carboxyalkylhydroxyalkylcellulose, carboxy methylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as osmogel), whereby they push the oxycodone or pharmaceutically acceptable salt thereof from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose possessing a 9,000 to 450,000 number-average molecular weight. The hydroxypropylalkylcellulose is represented by a member selected from the group consisting of hydroxypropylmethylcellulose, hydroxypropylethylcellulose, hydroxypropyl isopropyl cellulose, hydroxypropylbutylcellulose, and hydroxypropylpentylcellulose.

The push layer optionally may comprise a nontoxic colorant or dye. Examples of colorants or dyes include but are not limited to Food and Drug Administration Colorant (FD&C), such as FD&C No. 1 blue dye, FD&C No. 4 red dye, red ferric oxide, yellow ferric oxide, titanium dioxide, carbon black, and indigo.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain alternative embodiments, the dosage form comprises a homogenous core comprising oxycodone or a pharmaceutically acceptable salt thereof, the naloxone or pharmaceutically acceptable salt thereof, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc.). The homogenous core is surrounded by a semipermeable wall having a passageway (as defined above) for the release of the oxycodone or pharmaceutically acceptable salt thereof.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation as disclosed in U.S. Pat. Nos. 3,173,876; 3,276,586; 3,541,005; 3,541,006 and 3,546,876; semipermeable polymers as disclosed by Loeb and Sourirajan in U.S. Pat. No. 3,133,132; semipermeable crosslinked polystyrenes; semipermeable cross-linked poly(sodium styrene sulfonate); semipermeable crosslinked poly(vinylbenzyltrimethyl ammonium chloride); and semipermeable polymers possessing a fluid permeability of $2.5 \times 10^{-8}$ to $2.5 \times 10^{-2}$ (cm$^2$/hr·atm) expressed per atmosphere of hydrostatic or osmotic pressure difference across the semipermeable wall. Other polymers useful in the present invention are known in the art in U.S. Pat. Nos. 3,845,770; 3,916,899 and 4,160,020; and in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder. An example of a binder includes, but is not limited to a therapeutically acceptable vinyl polymer having a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinyl-pyrrolidone copolymers with a member selected from the group consisting of vinyl acetate, vinyl alcohol, vinyl chloride, vinyl fluoride, vinyl butyrate, vinyl laureate, and vinyl stearate. Other binders include for example, acacia, starch, gelatin, and hydroxypropylalkylcellulose of 9,200 to 250,000 average molecular weight.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

In certain preferred embodiments, the present invention includes a therapeutic composition comprising 10 to 40 mg of the oxycodone or pharmaceutically acceptable salt thereof, 25 to 500 mg of poly(alkylene oxide) having a 150,000 to 500,000 average molecular weight, 1 to 50 mg of polyvinylpyrrolidone having a 40,000 average molecular weight, 0 to about 7.5 mg of a lubricant and 0.80 to 0.90 mg of naloxone or salt thereof. The 0.80 to 0.90 mg of naloxone or salt thereof is preferably in the drug layer.

Suppositories

The sustained release formulations of the present invention may be formulated as a pharmaceutical suppository for rectal administration comprising a suitable suppository base, oxycodone (or oxycodone salt) and naloxone (or naloxone salt) in the dosages disclosed herein. Preparation of sustained release suppository formulations is described in, e.g., U.S. Pat. No. 5,215,758.

Prior to absorption, the drug must be in solution. In the case of suppositories, solution must be preceded by dissolution of the suppository base, or the melting of the base and subsequent partition of the drug from the suppository base into the rectal fluid. The absorption of the drug into the body may be altered by the suppository base. Thus, the particular suppository base to be used in conjunction with a particular drug must be chosen giving consideration to the physical properties of the drug. For example, lipid-soluble drugs will not partition readily into the rectal fluid, but drugs that are only slightly soluble in the lipid base will partition readily into the rectal fluid.

Among the different factors affecting the dissolution time (or release rate) of the drugs are the surface area of the drug substance presented to the dissolution solvent medium, the pH of the solution, the solubility of the substance in the specific solvent medium, and the driving forces of the saturation concentration of dissolved materials in the solvent medium. Generally, factors affecting the absorption of drugs from suppositories administered rectally include suppository vehicle, absorption site pH, drug pKa, degree of ionization, and lipid solubility.

The suppository base chosen should be compatible with the agents(s) of the present invention. Further, the suppository base is preferably non-toxic and nonirritating to mucous membranes, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata™ (types AB, AB, B, BC, BD, BBC, E, BCF, C, D and 299), manufactured by Henkel, and Witepsol™ (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of base (e.g., alginate) and drug used. Generally, the amount of suppository base is from about 20 percent to about 90 percent by weight of the total weight of the suppository. Preferably, the amount of suppository base in the suppository is from about 65 percent to about 80 percent, by weight of the total weight of the suppository.

Other Forms

The invention disclosed herein is meant to encompass all pharmaceutically acceptable salts thereof of the oxycodone and naloxone. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate, terephthalate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The combination of the oxycodone (or oxycodone salt) and the naloxone (or naloxone salt) can be employed in admixtures with conventional excipients, i.e., pharmaceutically acceptable organic or inorganic carrier substances suitable for oral administration, known to the art in order to provide a sustained release of at least the oxycodone or salt thereof. Suitable pharmaceutically acceptable carriers include but are not limited to, alcohols, gum arabic, vegetable oils, benzyl alcohols, polyethylene glycols, gelate, carbohydrates such as lactose, amylose or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, disintegrants, preservatives, stabilizers, wetting agents, emulsifiers, salts for influencing osmotic pressure buffers, coloring, flavoring and/or aromatic substances and the like. The compositions intended for oral use may be prepared according to any method known in the art and such compositions may contain one or more agents selected from the group consisting of inert, non-toxic pharmaceutically acceptable excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

The oral dosage forms of the present invention may be in the form of tablets, troches, lozenges, powders or granules, hard or soft capsules, microparticles (e.g., microcapsules, microspheres and the like), buccal tablets, suppositories, etc. The oxycodone (or oxycodone salt) and nalaxone (or nalaxone salt) may be substantially interdespersed with one another.

In certain embodiments, the present invention provides for a method of deterring parenteral abuse of an oral oxycodone dosage form (or oxycodone salt) by preparing the dosage forms as described above.

In certain embodiments, the present invention provides for a method of deterring diversion of an oral oxycodone dosage form comprising preparing the dosage forms as described above.

In certain embodiments, the present invention provides for a method of treating pain by administering to a human patient the dosage forms described above.

The following examples illustrate various aspects of the present invention. They are not to be construed to limit the claims in any manner whatsoever.

EXAMPLE 1

Sustained Release Oxycodone hydrochloride formulations containing naloxone hydrochloride are prepared with the formula in Table 1 below:

TABLE 1

| Ingredients | Amt/Unit (mg) | Amount/Batch (gm) |
|---|---|---|
| Oxycodone HCl | 20.0 | 200.0 |
| Spray Dried Lactose | 59.25 | 592.5 |
| Povidone | 5.0 | 50.0 |
| Eudragit RS30D (solids) | 10.0 | 100 |
| Triacetin | 2.0 | 20.0 |
| Naloxone HCl Dihydrate | 0.85 | 8.50 |
| Stearyl Alcohol | 25.0 | 250.0 |
| Talc | 2.5 | 25.0 |
| Magnesium Stearate | 1.25 | 12.5 |
| 4% Moisture | 5.0 | 50.0 |
| Opadry Pink Y-S-14518A | 5.0 | 50.0 |
| Total | 135.85 | 1358.5 |

In this example, the naloxone hydrochloride dihydrate is added to the formulation during the granulation process. The process is set forth below:
1. Dispersion: Naloxone HCl is dissolved in water and the solution is added to a Eudragit/Triacetin dispersion.
2. Granulation: Spray the Eudragit/Triacetin dispersion onto an Oxycodone HCl, Spray Dried Lactose and Povidone mixture using a fluid bed granulator.
3. Milling: Discharge the granulation and pass through a mill with approximately 1 mm openings (18 mesh screen).
4. Waxing: Melt the stearyl alcohol at about 50 degrees C. and add to the milled granulation using a high shear mixer. Allow to cool at room temperature on trays or a fluid bed.
5. Milling: Pass the cooled granulation through a mill with approximately 18 mesh screen.
6. Lubrication: Lubricate the granulation with talc and magnesium stearate using a mixer.
7. Compression: Compress the granulation into tablets using a Kilian® tablet press.
8. Film Coating: Apply an aqueous film coat to the tablets using a rotary pan.

EXAMPLE 2

Oxycodone salt/naloxone salt sustained release osmotic tablets are produced with the formula set forth in Table 2 below:

TABLE 2

| Ingredient | Amt/unit (mg) |
|---|---|
| Drug Layer: | |
| Oxycodone HCl | 20.0 |
| Naloxone HCL Dihydrate | 0.85 |
| Polyethylene oxide | 130.24 |
| Povidone | 8.8 |
| Magnesium Stearate | 1.76 |
| Displacement Layer: | |
| Polyethylene oxide | 85.96 |
| Sodium chloride | 40.50 |
| Hydroxypropylmethylcellulose | 6.75 |
| Ferric Oxide | 1.35 |
| Magnesium Stearate | 0.34 |
| BHT | 0.10 |
| Semipermeable Wall: | |
| Cellulose acetate | 38.6 |

The dosage form having the above formulation is prepared according to the following procedure:

First, the oxycodone hydrochloride, the naloxone hydrochloride dihydrate, poly(ethylene oxide) possessing a 200,000 average molecular weight, and polyvinylpyrrolidone having a 40,000 average molecular weight is added to a mixer and mixed for 10 minutes. Then, denatured anhydrous alcohol is added to the blended materials with continuous mixing for 10 minutes. Then, the wet granulation is passed through a 20 mesh screen, allowed to dry at room temperature for 20 hours, and then passed through a 16 mesh screen. Next, the granulation is transferred to the mixer, mixed and lubricated with magnesium stearate.

Then, the displacement or push composition for pushing the oxycodone HCl/naloxone HCL composition from the dosage form is prepared as follows: first 3910 g of hydroxypropylmethylcellulose possessing a 11,200 average molecular weight is dissolved in 45,339 g of water. Then, 101 g of butylated hydroxytoluene is dissolved in 650 g of denatured anhydrous alcohol. Next, 2.5 kg of the hydroxypropylmethylcellulose aqueous solution is added with continuous mixing to the butylated hydroxytoluene alcohol solution. Then, binder solution preparation is completed by adding with continuous mixing the remaining hydroxypropylmethylcellulose aqueous solution to the butylated hydroxytoluene alcohol solution.

Next, 36,000 g of sodium chloride is sized using a Quadro Comil® mill equipped with a 21 mesh screen. Then, 1200 g of ferric oxide is passed through a 40 mesh screen. Then, the screened materials, 76,400 g of pharmaceutically acceptable poly(ethylene oxide) possessing a 7,500,000 average molecular weight, 2500 g of hydroxypropylmethylcellulose having a 11,200 average molecular weight are added to a Glatt® Fluid Bed Granulation's bowl. The bowl is attached to the granulator and the granulation process is initiated for effecting granulation. Next, the dry powders are air suspended and mixed for 10 minutes. Then, the binder solution is sprayed from 3 nozzles onto the powder. The granulating is monitored during the process as follows: total solution spray rate of 800 g/min; inlet temperature 43° C. and air flow 4300 m³/hr. At the end of solution spraying, 45,033 g, the resultant coated granulated particles are subjected to a drying process for 35 minutes.

The coated granules are sized using a Quadro Comil® mill with an 8 mesh screen. The granulation is transferred to a Tote® Tumbler, mixed and lubricated with 281.7 g of magnesium stearate.

Next, the drug composition comprising the oxycodone hydrochloride/naloxone hydrochloride and the push composition are compressed into bilayer tablets on a Kilian® Tablet press. First, the drug composition is added to the die cavity and precompressed, then, 135 mg of the push composition is added and the layers are pressed under a pressure head of 3 metric tons into a ¹¹⁄₃₂ inch (0.873 cm) diameter contacting layer arrangement.

The bilayered arrangements are coated with a semipermeable wall. The wall forming composition comprises 100% cellulose acetate having a 39.8% acetyl content. The wall-forming composition is dissolved in acetone:water (95:5 wt:wt) cosolvent to make a 4% solid solution. The wall-forming composition is sprayed onto and around the bilayers in a 24 inch (60 cm) Vector® Hi-Coater. Next, one 20 mil (0.508 mm) exit passageway is drilled through the semipermeable wall to connect the drug oxycodone layer with the exterior of the dosage form. The residual solvent is removed by drying for 72 hours at 45° C. and 45% humidity. Next, the osmotic dosage systems are dried for 4 hours at 45° C. to remove excess moisture.

EXAMPLE 3

Oxycodone 10 mg/naloxone 0.85 mg sustained release capsules are prepared with the formula set forth in Table 4 below:

TABLE 4

| Ingredient | Amt/unit (mg) |
| --- | --- |
| Oxycodone HCl | 10.0 |
| Naloxone HCl dihydrate | 0.85 |
| Stearic Acid | 8.15 |
| Stearic Alcohol | 24.00 |
| Eudragit RSPO | 77 |
| Total | 120 |

The formulation above is prepared according to the following procedure:
1. Pass the stearyl alcohol flakes through an impact mill.
2. Blend the Oxycodone HCl, Naloxone HCl, stearic acid, stearyl alcohol and the Eudragit RSPO in a suitable blender/mixer.
3. Continuously feed the blended material into a twin screw extruder at elevated temperatures, and collect the resultant strands on a conveyor.
4. Allow the strands to cool on the conveyor.
5. Cut the strands into 1 mm pellets using a pelletizer.
6. Screen the pellets for fines and oversized pellets to an acceptable range of about 0.8-1.4 mm in size.
7. Fill into capsules with a fill weight of 120 mg/capsule (fill into size 2 capsules).

EXAMPLE 4

Oxycodone 10 mg/naloxone 0.85 mg sustained release capsules are prepared according to the following procedure:
Initially, immediate release oxycodone beads are prepared with the formula set forth in Table 5 below:

TABLE 5

| Ingredients | Amount/Unit (mg) |
| --- | --- |
| Oxycodone HCl | 10.0 |
| Opadry ® Clear YS-1-19025A | 1.25 |
| NuPareil (Sugar beads) 30/35 mesh | 54.35 |
| Opadry ® Butterscotch YS-1-17307A | 1.90 |
| Total | 62.5 |

Process
1. Drug layering solution: Dissolve oxycodone HCl and Opadry Clear in water.
2. Drug loading: Spray the drug solution onto NuPareil beads in a fluid bed dryer.
3. Coating: Disperse Opadry Butterscotch in water. Spray onto the drug loaded beads.
   Sustained Release Beads are then prepared with the formula set forth in Table 6 below:

TABLE 6

| Ingredients | Amount/Unit (mg) |
| --- | --- |
| Oxycodone IR Beads (5 mg/62.5 mg) | 53.08 |
| Eudragit ® RS 30 D (solids) | 5.04 |
| Eudragit ® RL 30 D (solids) | 0.27 |
| Triethyl Citrate | 1.05 |
| Cab-O-Sil ® | 0.27 |
| Opadry ® Clear YS-1-19025A | 2.79 |
| Total | 62.5 |

Process
1. Controlled release coating solution: Homogenize triethyl citrate in water. Add the dispersion to Eudragit®RS 30 D and Eudragit®RL 30 D then add Cab-O-Sil® to mixture.
2. Seal coat solution: Dissolve Opadry® Clear in water.
3. Coating: Apply the control release coating solution followed by the seal coat solution onto Oxycodone HCl IR beads using a fluidized bed bottom-spray technique.
4. Curing: Place the coated beads on tray and cure in oven for 24 hours at 45° C.

To develop Oxycodone/Naloxone sustained release beads 0.85 mg of Naloxone per unit can be included in the above formulation. It can be dissolved together with the Oxycodone HCl in the purified water before being sprayed onto the NuPareil beads.

EXAMPLE 5

Sustained release 10 mg oxycodone hydrochloride formulations containing naloxone hydrochloride were prepared with the formula in Table 7 below:

TABLE 7

| Ingredients | Amt/Unit (mg) | Amount/Batch (kg) |
| --- | --- | --- |
| Oxycodone HCl | 10.00 | 11.00 |
| Spray Dried Lactose | 68.40 | 75.3 |
| Povidone | 5.00 | 5.5 |
| Eudragit RS30D (solid) | 10.00 | 11.0* |
| Triacetin | 2.00 | 2.2 |
| Naloxone HCl Dihydrate | 0.85 | 0.936 |
| Stearyl Alcohol | 25.00 | 27.5 |
| Talc | 2.50 | 2.8 |
| Magnesium Stearate | 1.25 | 1.4 |
| 4% Residual Moisture | 5.00 | 5.5 |
| Opadry White Film Y-5-18024-A | 5.00 | 5.5 |
| Total | 135.00 | 148.6 |

*utilized as 36.7 kg of an aqueous dispersion

The formulation in Table 7 was prepared according to the following procedure:
1. Blend Oxycodone HCl, Lactose and a portion of Povidone in Niro MP-6 Fluid Bed Processor (Glatt GPCG-60/120 may be substituted).
2. Mix Eudragit®RS30D and Triacetin in a stainless steel vessel using a Lightin' Air mixer.
3. Granulate the blend from Step 1 in the Niro MP-6 (or Glatt GPCG-60/120) Fluid Bed Processor by spraying the Eudragit® dispersion from Step 2.
4. Mix remaining Povidone, Naloxone HCl and water to form a clear solution in a stainless steel vessel using a Lightin' Air mixer.
5. Spray Naloxone HCl solution from Step 4 onto granulation from Step 3 in the Niro MP-6 (or Glatt GPCG-60/120) Fluid Bed Processor.
6. Screen the granulation from Step 5 using a Quadro Comil.
7. Incorporate Stearyl Alcohol (previously melted in a steam-jacketed kettle) with screened granulation from Step 6 in a Collette Granulator/Mixer.
8. Cool the waxed granulation from Step 7 in the Niro MP-6 (or Glatt GPCG-60/120) Fluid Bed Processor, or, alternatively, on stainless steel trays.
9. De-lump cooled granulation from Step 8 using a Quadro Comil.
10. Blend granulation from Step 8 with Talc and Magnesium Stearate in the Collette Granulator/Mixer.
11. Compress granulation into tablets using a Kilian S-250 Tablet Press.
12. Coat Tablets with Opadry in a 48" Accela-Cota Coating Pan.

The tablets were then tested for dissolution using the USP Apparatus I (Basket) method of U.S. Pharmacopeia XXIV (2000) at 100 rpm in 900 ml simulated gastric fluid (SGF) at 37° C.

The dissolution results are set forth in Table 7A below:

TABLE 7A

| Time (hour) | % of Oxycodone Released | % of Naloxone Released |
|---|---|---|
| 1 | 37 | 39 |
| 2 | 52 | 54 |
| 4 | 68 | 70 |
| 8 | 87 | 86 |
| 12 | 97 | 96 |

EXAMPLE 6

Sustained release 20 mg oxycodone hydrochloride formulations containing naloxone hydrochloride were prepared with the formula in Table 8 below:

TABLE 8

| Ingredients | Amt/Unit (mg) | Amount/Batch (kg) |
|---|---|---|
| Oxycodone HCl | 20.00 | 22.0 |
| Spray Dried Lactose | 58.40 | 64.3 |
| Povidone | 5.00 | 5.5 |
| Eudragit RS30D (solid) | 10.00 | 11.0* |
| Triacetin | 2.00 | 2.2 |
| Naloxone HCl Dihydrate | 0.85 | 0.936 |
| Stearyl Alcohol | 25.00 | 27.5 |
| Talc | 2.50 | 2.8 |
| Magnesium Stearate | 1.25 | 1.4 |
| 4% Residual Moisture | 5.00 | 5.5 |
| Opadry Pink Y-S-1-14518A | 5.00 | 5.5 |
| Total | 135.00 | 148.6 |

*utilized as 36.7 kg of an aqueous dispersion

The formulation in Table 8 was prepared according to the same procedure as in Example 5.

The tablets were then tested for dissolution using the USP Apparatus I (Basket) method of U.S. Pharmacopeia XXIV (2000) at 100 rpm in 900 ml simulated gastric fluid (SGF) at 37° C.

The dissolution results are set forth in Table 8A below:

TABLE 8A

| Time (hour) | % of Oxycodone Released | % of Naloxone Released |
|---|---|---|
| 1 | 41 | 43 |
| 2 | 57 | 60 |
| 4 | 75 | 77 |
| 8 | 93 | 94 |
| 12 | 100 | 101 |

EXAMPLE 7

Sustained release 40 mg oxycodone hydrochloride formulations containing naloxone hydrochloride were prepared with the formula in Table 9 below:

TABLE 9

| Ingredients | Amt/Unit (mg) | Amount/Batch (kg) |
|---|---|---|
| Oxycodone HCl | 40.00 | 44.0 |
| Spray Dried Lactose | 34.40 | 37.9 |
| Povidone | 5.00 | 5.5 |
| Eudragit RS30D (solid) | 14.00 | 15.4 |
| Triacetin | 2.00 | 2.2 |
| Naloxone HCl Dihydrate | 0.85 | 0.936 |
| Stearyl Alcohol | 25.00 | 27.5 |
| Talc | 2.50 | 2.8 |
| Magnesium Stearate | 1.25 | 1.4 |
| 4% Residual Moisture | 5.00 | 5.5 |
| Opadry Yellow Y-S-1-12525-A | 5.00 | 5.5 |
| Total | 135.00 | 148.6 |

*utilized as 51.4 kg of an aqueous dispersion

The formulation in Table 9 was prepared according to the same procedure as in Example 5.

The tablets were then tested for dissolution using the USP Apparatus I (Basket) method of U.S. Pharmacopeia XXIV (2000) at 100 rpm in 900 ml simulated gastric fluid (SGF) at 37° C.

The dissolution results are set forth in Table 9A below:

TABLE 9A

| Time (hour) | % of Oxycodone Released | % of Naloxone Released |
|---|---|---|
| 1 | 45 | 47 |
| 2 | 61 | 63 |
| 4 | 79 | 80 |
| 8 | 97 | 97 |
| 12 | 103 | 102 |

EXAMPLE 8

In Example 8, a single-center, open-label, randomized, 4-period, 4-sequence, 4-treatment crossover study in 18 normal, healthy, young adult, male and female subjects under fasted conditions was conducted. The study was conducted to compare the pharmacokinetic parameters of naloxone in a single tablet dose of Talwin® Nx (containing ~0.55 mg naloxone hydrochloride), 1.5 mg oral naloxone hydrochloride as a single dose, 1.5 mg oral naloxone hydrochloride as divided doses (0.75 mg, ~0.25 mg, ~0.25 mg, and ~0.25 mg at times 0, 3, 6, and 9 hours respectively), and 0.5 mg of 0.4 mg/ml intravenous naloxone hydrochloride. Subjects were randomly assigned to four sequences with periods consisting of the following:

Period 1 was Days 1-8 (from the time of the first dose until the time of the second dose),
Period 2 was Days 8-15 (from the time of the second dose until the third dose),
Period 3 was Days 15-22 (from the third dose until the fourth dose), and
Period 4 was Days 22 (from the time of the last dose until the end of the study).

The randomization sequences of administration are listed in Table 10 below:

TABLE 10

|  | Period 1 | Period 2 | Period 3 | Period 4 |
|---|---|---|---|---|
| Sequence 1 | Talwin ® Nx | Oral Nx-1 dose | Oral Nx divided | IV Nx |

TABLE 10-continued

|  | Period 1 | Period 2 | Period 3 | Period 4 |
|---|---|---|---|---|
| Sequence 2 | IV Nx | Talwin ® Nx | Oral Nx-1 dose | Oral Nx divided |
| Sequence 3 | Oral Nx divided | IV Nx-1 dose | Talwin ® Nx | Oral Nx-1 dose |
| Sequence 4 | Oral Nx-1 dose | Oral Nx divided | IV Nx | Talwin ® Nx |

Nx = naloxone. Oral Nx was administered as a single 1.5 mg solution or in divided doses of 0.75, ~0.25, ~0.25, and ~0.25 at times 0, 3, 6, and 9 h respectively.

Subjects were admitted to the study facility on the evenings of Days 0, 7, 14 and 21, at least 12 hours prior to dosing and were confined until at least 6 hours after dosing (and at least 12 hours after dosing for the group receiving divided doses of oral naloxone HCl). Dosing took place on Days 1, 8, 15, and 22. For the duration of the study, subjects were instructed not to engage in heavy exercise.

Stock solutions and medications used in the study consisted of 2 ml vials of 1 mg/ml naloxone HCl injection USP purchased from Sabex Inc., 10 ml vials of 0.4 mg/ml naloxone HCl injection USP purchased from Sabex Inc., and Talwin® Nx (tablets of pentazocine and naloxone hydrochloride, USP, equivalent to 50 mg base and 0.5 mg base respectively. The 1 mg/ml naloxone concentration was used for an intravenous naloxone challenge test at screening, and the 0.4 mg/ml concentration was used for intravenous dosing during the study. For oral dosing, the 1 mg/ml stock was diluted with water to 0.02 mg/ml. Doses were as follows: 1 tablet of Talwin® Nx, 0.5 mg intravenous naloxone HCl (1.25 ml of 0.4 mg/ml), 1.5 mg of oral naloxone HCl as a single 75 ml oral dose (concentration of 0.02 mg/ml), and 1.5 mg of naloxone HCl as divided oral doses with 50% (0.75 mg), 17% (~0.25 mg), 17% (~0.25 mg), and 16% (~0.25 mg) of the dose administered at time 0, 3, 6, and 9 hours respectively.

Talwin® Nx was administered with 8 ounces of water, which the subjects drank completely. Afterwards, mouth inspections were done to ensure that each subject swallowed the tablet.

Following the single oral dose of naloxone, subjects drank two additional 75 ml rinses of water, for a total volume of 225 ml. For divided doses (also 0.02 mg/ml), the first dose was followed by two 94 ml rinses of water, and subsequent doses were followed by two 75 ml rinses of water.

Intravenous naloxone was administered by IV push. Following IV naloxone, subjects were observed by staff members continuously for at least 20 minutes.

Each subject received each treatment one time. Each treatment followed an overnight fast (excluding water) of at least 10 hours, and after dosing, the subjects fasted for an additional 4 hours. Except for the days of dosings, there were no food restrictions. While subjects were confined to the clinical unit all meals were served at standardized times, and the content was standardized throughout the study and between subjects. Meal records were maintained, including content. No caffeine or xanthine-containing beverages were served while the subjects were in the clinical facility.

In the study, 17 of the 18 randomized subjects completed all four treatments. One subject randomized to sequence 4 withdrew consent after completing the first treatment phase (single-dose oral naloxone).

Pharmacokinetic Results

A summary of the Pharmacokinetic data ($AUC_t$, $AUC_{0-\infty}$, $C_{max}$, $t_{1/2}$, $t_{max}$, Cl and $V_{ss}$ were done) for the study is listed in Table 11 below:

TABLE 11

| | Arithmetic Mean (SD); N = 17 | | | |
|---|---|---|---|---|
| Metric | 0.5 mg IV Naloxone HCl | 1.5 mg Naloxone HCl (oral divided doses) | 1.5 mg Naloxone HCl (single oral dose) | Talwin ® Nx (0.55 mg Naloxone HCl) |
| $AUC_t$ (pg · h/ml) | 3199 (820) | 64.9 (57.6) | 47.4 (32.3)[b] | 5.92 (7.21) |
| $AUC_{0-\infty}$ (pg · h/ml) | 3051 (668)[a] | —[c] | —[c] | —[e] |
| $C_{max}$ (pg/ml) | 6252 (4482) | 13.4 (7.02) | 23.0 (13.3)[b] | 8.00 (5.13) |
| $t_{max}$ (h) | 0.14 (0.35) | 3.18 (3.81) | 0.78 (1.07)[b] | 0.71 (1.14) |
| $t_{1/2}$ (h) | 0.92 (0.11)[a] | —[c] | —[c] | —[e] |
| Cl (ml/min) | 2854 (612)[a] | —[d] | —[d] | —[d] |
| $V_{ss}$ (L) | 217 (45.5)[a] | —[d] | —[d] | —[d] |

Cl: Plasma clearance estimated as the ratio ($Dose/AUC_{0-\infty}$)
$V_{ss}$: Volume of distribution at steady-state estimated as the ratio ($Dose*AUMC_{0-\infty}$)/($AUC_{0-\infty}$)[2] where $AUMC_{0-\infty}$ is the area under the curve of the product of time and drug concentration from time zero to infinity (first moment of the plasma concentration-time curve).
[a]15 subjects-Subjects 9 and 15 could not be used.
[b]18 subjects
[c]$t_{1/2}$ and $AUC_{0-\infty}$ could not be estimated/reported for 15 of the 17 subjects
[d]Cl and $V_{ss}$ were calculated for the IV treatment arm only
[e]$t_{1/2}$ and $AUC_{0-\infty}$ could not be estimated/reported for any of the 17 subjects Table 12 below lists a summary of the Pharmacokinetic data which is Dose Normalized to 0.5 mg IV Naloxone HCl dose.

TABLE 12

| | Arithmetic Mean (SD); N = 17 | | | |
|---|---|---|---|---|
| Metric | 0.5 mg IV Naloxone HCl | 1.5 mg Naloxone HCl (oral divided doses) | 1.5 mg Naloxone HCl (single oral dose) | Talwin ® Nx (0.55 mg Naloxone HCl) |
| $AUC_t$ (pg · h/ml) | 3199 (820) | 21.6 (19.2) | 15.8 (10.8)[b] | 5.38 (6.56) |
| $AUC_{0-\infty}$ (pg · h/ml) | 3051 (668)[a] | —[c] | —[c] | —[d] |
| $C_{max}$ (pg/ml) | 6252 (4482) | 4.47 (2.34) | 7.68 (4.43)[b] | 7.27 (4.67) |
| F (%) | — | 0.66 (0.59) | 0.47 (0.28) | 0.17 (0.22) |
| F (%)-Range | — | 0.01-2.08 | 0.15-1.11 | 0.00-0.79 |

F: Absolute Bioavailability, estimated as the ratio of the dose-normalized $AUC_t$ of the selected treatment and the $AUC_{0-\infty}$ from the IV treatment arm. If AUG for the IV treatment was NE (not estimable), $AUC_t$ was used.
[a]15 subjects
[b]18 subjects
[c]$t_{1/2}$ and $AUC_{0-\infty}$ could not be estimated/reported for 15 of the 17 subjects
[d]$t_{1/2}$ and $AUC_{0-\infty}$ could not be estimated/reported for any of the 17 subjects Arithmetic mean observed plasma concentration-time profiles for naloxone for the four treatment arms are presented in FIGS. 2A-D. Spaghetti plots of the observed individual plasma concentration-time profiles for naloxone for the four treatment arms are presented in FIGS. 3A-D. A rapid increase to naloxone peak plasma concentrations was observed for all four treatments tested. The time to peak plasma concentrations was, as expected, lowest for the IV formulation (0.14 h, ~9 min) followed by Talwin® Nx (0.71 h), the single oral solution dose of naloxone (0.78 h), and finally the divided oral doses of naxolone (3.18 h). Mean peak plasma exposures ($C_{max}$) of 6252 pg/ml, 23.0 pg/ml, 13.4 pg/ml, and 8.00 pg/ml were observed for 0.5 mg IV naloxone HCl, 1.5 mg single oral dose of naloxone HCl, 1.5 mg divided oral doses of naloxone HCl and Talwin® Nx (containing 0.55 mg of naloxone HCl), respectively.

The mean apparent terminal elimination half-life ($t_{1/2}$) for the IV treatment arm was 0.92 h. The terminal portion of the plasma concentration time curves 9 and 15 could not be used to determine the half-life values). The terminal elimination half-life was not estimable for the three oral treatments (since λ the apparent terminal elimination rate constant, could not be accurately determined based on "saw tooth" concentration time profiles of the majority of the subjects).

Mean total naloxone exposure ($AUC_t$) of the 1.5 mg single oral dose (47.4 pg·h/ml) was approximately 73% of the 1.5 mg divided oral doses of naloxone (64.9 pg·h/ml). The 0.5 mg IV dose of naloxone, as expected, produced the highest mean total exposure of 3199 pg·h/ml while the Talwin® Nx treatment produced a mean total exposure value of 5.92 pg·h/ml. The mean total exposure ($AUC_{0-\infty}$) extrapolated to infinity for the 0.5 mg IV treatment arm was 3051 pg·h/ml while $AUC_{0-\infty}$ was not estimable for the three oral treatments since terminal elimination half-life could not be estimated for 15 of the 17 subjects.

Mean plasma clearance and volume of distribution at steady-state were estimated to be 2854 ml/min and 217 L, respectively, for the IV treatment arm.

Mean absolute bioavailability ($F_t$) (based on $AUC_t$) of the single oral dose of 1.5 mg naloxone HCl was 0.47% (range: 0.15-1.11%), that of the divided oral doses of 1.5 mg naloxone HCl was 0.66% (range: 0.01-2.08%), and that of the single tablet dose of Talwin® Nx (containing 0.55 mg of naloxone HCl) was 0.17% (range: 0.0-0.79%). These low bioavailability values reflect the significant first pass metabolism that occurs when naloxone is administered orally.

Overall, there was significant variability, in terms of % CV, associated with the naloxone $C_{max}$ values across all treatments range: 52-72%. The $AUC_t$ values were less variable for the IV treatment, % CV-26%, where as the oral treatments were highly variable % CV range: 68-122%.

Adverse Events

There were no deaths or serious adverse events. No subjects discontinued because of adverse events. The majority of drug-related adverse events occurred when subjects were dosed with Talwin® Nx. These included nausea, vomiting, dizziness, and headache. One subject withdrew consent due to a schedule conflict.

Eleven of 18 subjects experienced a total of 25 adverse events, none serious. Seven of these subjects experienced adverse events described as possibly, probably, or definitely related to the study medication. Overall, adverse events were more frequently reported in subjects receiving Talwin® Nx, consistent with expected adverse events related to pentazocine. All subjects recovered from all adverse events. No action (e.g., discontinuation) was taken with regard to the study drug.

Following dosing with Talwin® Nx, 6 subjects reported adverse events, all described as probably or definitely related to the study medication, including dizziness (N=5), nausea (N=2), vomiting (N=1), and fatigue (N=1). Severe adverse events among subjects receiving Talwin® Nx including dizziness (N=1) and nausea (N=2).

During the other three treatments, no subjects reported severe adverse events which were possibly, probably, or definitely related to study medication and no subjects reported dizziness or any severity. Also during the other three treatment groups, only two adverse events were considered possibly, probably, or definitely related to study drug: headache possibly related to oral naloxone in divided doses, and nausea possibly related to intravenous naloxone. No adverse events were observed during the naloxone challenge test among the 18 subjects randomized.

The most commonly reported adverse events were dizziness and headache. Headache was reported by 5 subjects, none during the Talwin® Nx dosing period. For 1 of the subjects, headache occurred prior to randomization, for 3 subjects it occurred during only 1 treatment period, and for 1 subject it occurred during 2 periods. It was considered possibly, probably, or definitely related to study drug in only 1 subject, after oral naloxone in divided doses, and the severity was mild. None of the other subjects reported the onset of headache on a dosing day after administration of study drug.

Conclusions from the Study

The absolute bioavailability of naloxone was <1% for all three oral treatments studied. Plasma naloxone concentrations were highly variable for all treatments. Mean naloxone peak exposure was 8 pg/ml, range 0-16.6 pg/ml, approximately 0.1% of that following i.v. administration of naloxone. The terminal half-life of naloxone was short, approximately 1 h.

Naloxone, HCl given alone is well tolerated at total doses of 0.5 mg IV and up to 1.5 mg orally.

EXAMPLE 9

In Example 9, a single-dose, randomized, open-label, 2-period, 2-treatment crossover study in normal, healthy, adult, male and female subjects conducted to assess the bioequivalence of OxyContin® 40 mg and the oxycodone/naloxone controlled-release dosage form (40 mg/0.85 mg) of Example 7 was performed. Up to 96 subjects were to be enrolled in order to complete a minimum of 48 subjects who were evaluable for pharmacokinetics. Subjects satisfying the screening requirements were admitted to the study center on Day-1 and underwent a Narcan® (naloxone hydrochloride solution) challenge test on Day 1. Subjects successfully completing the Narcan® challenge were randomly assigned to 1 of 2 crossover treatment sequences (reference to test or test to reference) with a 5-day washout period separating dosing in the 2 periods. Subjects were confined to the study facility continuously from Day-1 until Day 10. Subjects were dosed with one of the treatments at approximately 8:00 AM on Days 2 and 7, per the randomization code. All doses were administered with 8 ounces of water after an overnight fast (excluding water). Following dosing on Days 2 and 7, serial blood samples were collected over the interval from predose to 72 hours postdose. Plasma concentrations of oxycodone and naloxone (as applicable) were determined, and pharmacokinetic metrics were calculated and analyzed. Safety measurements consisted of reports of adverse events, vital sign measurements, pulse oximetry, clinical laboratory parameters, electrocardiograms (ECG), and physical examinations. For the purpose of statistical analyses, Period 1 was defined as the time from administration of the first dose (Day 2) to just prior to administration of the second dose (Day 7). Period 2 was defined as the time from administration of the second dose (Day 7) to the time of the 72-hour postdose blood collection on Day 10. Evaluable subjects (in terms of bioequivalence assessments) must have not had any incidence of emesis for at least 12 hours following each of the 2 study treatment.

Pharmacokinetic metrics (mean±SD) for oxycodone controlled-release with naloxone and OxyContin® are summarized in Table 13 below. For each pharmacokinetic metric determined and calculated, mean values were similar following test and reference treatments and arithmetic means (±SD) of all parameters were within approximately 10% of each other.

TABLE 13

Summary of Oxycodone Pharmacokinetic Metrics: PK Population

| | | Arithmetic Mean ± SD | | |
|---|---|---|---|---|
| Metric | N | Test Oxycodone Controlled-Release with Naloxone | N | Reference OxyContin ® |
| $AUC_t$ (ng · h/mL) | 66 | 504.85 ± 126.81 | 67 | 535.23 ± 143.39 |
| $AUC_\infty$ (ng · h/mL) | 65 | 510.03 ± 127.74 | 66 | 542.47 ± 143.66 |
| $C_{max}$ (ng/mL) | 66 | 44.79 ± 10.67 | 67 | 43.61 ± 11.71 |
| $t_{max}$ (h) | 66 | 3.49 ± 1.47 | 67 | 3.98 ± 2.36 |
| $t_{1/2}$ (h) | 65 | 6.22 ± 3.07 | 66 | 6.47 ± 2.99 |

Subject 21 was dosed with oxycodone controlled-release with naloxone in both periods in error.
Metrics from Subject 21 are excluded from this analysis because the subject had emesis in both periods prior to 12 hours.

Pharmacokinetic metrics (mean±SD) for naloxone are summarized in Table 14 below.

TABLE 14

Summary of Naloxone Pharmacokinetic Metrics: PK Population

| | | Arithmetic Mean ± SD |
|---|---|---|
| Metric | N | Naloxone (N = 66) |
| $AUC_t$ (pg · h/mL) | 65 | 2.95 ± 11.163 |
| $C_{max}$ (pg/mL) | 66 | 2.13 ± 4.466 |
| $t_{max}$ (h) | 17 | 3.35 ± 3.694 |
| $t_{1/2}$ (h) | 2 | 4.30 ± 3.026 |

Subject 21 was dosed with oxycodone controlled-release with naloxone in both periods in error.
Metrics from Subject 21 are excluded from this analysis because the subject had emesis in both periods prior to 12 hours.

The bioequivalence of oxycodone controlled-release with naloxone (test) versus Oxycontin® (reference was assessed using bioequivalence criteria based on the LS (least squares) mean AUC and $C_{max}$ values for each treatment are listed in Table 15 below. Confidence intervals (90%) around the ratios of exponentiated LS means for $C_{max}$ and AUC values are also presented in Table 15 below.

TABLE 15

Summary of Oxycodone $AUC_t$, $AUC_\infty$, and $C_{max}$ Means, Ratios, and Confidence Intervals by Treatment

| | Test Oxycodone controlled-release with naloxone (N = 66) | Reference Oxy-Contin ® (N = 67) | Ratio (%) | 90% CI |
|---|---|---|---|---|
| Pharmacokinetic Metric | | | | |
| $AUC_t$ (ng · h/mL) | | | | |
| N | 66 | 67 | | |
| Geometric Mean | 489.27 | 516.32 | | |
| Exponentiated LS Mean | 489.03 | 505.90 | 96.66 | 93.50, 99.94 |
| $AUC_\infty$ (ng · h/mL) | | | | |
| N | 65 | 66 | | |
| Geometric Mean | 494.30 | 523.69 | | |
| Exponentiated LS Mean | 495.45 | 513.52 | 96.48 | 93.28, 99.80 |
| $C_{max}$ (ng/mL) | | | | |
| N | 66 | 67 | | |
| Geometric Mean | 43.61 | 42.23 | | |
| Exponentiated LS Mean | 43.26 | 41.64 | 103.89 | 100.13, 107.79 |

Subject 21 was dosed with oxycodone controlled-release with naloxone in both periods in error.
Metrics from Subject 21 are excluded from this analysis because the subject had emesis in both periods prior to 12 hours.
Log-transformed parameters were used in calculating the ratio and 90% CI and then exponentiated back. The ratio and 90% CI were based on exponentiated LS means with effects for sequence, subject (sequence), period, and treatment in the ANOVA model.

As can be seen from the table above, for $AUC_t$, $AUC_\infty$, and $C_{max}$, the upper limit of the 90% confidence intervals of the ratios was less than 125% (100%, 100%, and 108% for $AUC_t$, $AUC_\infty$, and $C_{max}$, respectively), while the lower limit of the 90% confidence intervals of the ratios was above 80% (94%, 93%, and 100% for $AUC_t$, $AUC_\infty$, and $C_{max}$, respectively). These results indicate that 40 mg oxycodone controlled-release with naloxone is bioequivalent to 40 mg OxyContin®.

Safety Analysis

The safety parameters in this study were consistent with parameters utilized to assess safety in Phase 1 studies of opioids. Overall, oxycodone controlled-release with naloxone was well tolerated by healthy subjects. There were no deaths or serious adverse events reported. Two subjects were discontinued from the study because of adverse events. The most common adverse events were pruritus, nausea, dizziness, somnolence, and vomiting. All adverse events were mild to moderate in intensity. All adverse events, with the exception of an adverse event for one subject (whose increased cough was not considered related to study drug and continued after the end of the study), resolved by the completion of the study. All study drug-related adverse events were consistent with the known safety profile of oxycodone. Changes in clinical laboratory values were sporadic and considered to be unrelated to study medication. There were no clinically meaningful drug-related changes in physical examinations, vital signs, or electrocardiograms (ECGs).

The overall incidence of adverse events (greater than 10%) is presented in Table 16 below.

TABLE 16

Common Adverse Events (Incidence >10% for Any Treatment) by Body System and COSTART (Coding Symbols for Thesaurus of Reaction Terms) Term: Safety Population

| Body System/COSTART Term | Test Oxycodone controlled-release with naloxone (N = 93) n (%) | Reference OxyContin ® (N = 94) n (%) |
|---|---|---|
| Total number (%) of subjects with adverse events | 85 (91.4%) | 85 (90.4%) |

TABLE 16-continued

Common Adverse Events (Incidence >10% for Any Treatment) by Body System and COSTART (Coding Symbols for Thesaurus of Reaction Terms) Term: Safety Population

| Body System/COSTART Term | Test Oxycodone controlled-release with naloxone (N = 93) n (%) | Reference OxyContin ® (N = 94) n (%) |
|---|---|---|
| Body as a Whole | | |
| Headache | 22 (23.7%) | 21 (22.3%) |
| Cardiovascular System | | |
| Vasodilatation | 23 (24.7%) | 14 (14.9%) |
| Digestive System | | |
| Nausea | 45 (48.4%) | 35 (37.2%) |
| Vomiting | 31 (33.3%) | 29 (30.9%) |
| Nervous System | | |
| Dizziness | 34 (36.6%) | 43 (45.7%) |
| Euphoria | 29 (31.2%) | 25 (26.6%) |
| Somnolence | 39 (41.9%) | 37 (39.4%) |
| Skin and Appendages | | |
| Pruritus | 49 (52.7%) | 47 (50.0%) |
| Sweating | 10 (10.8%) | 8 (8.5%) |

Following each treatment, 85 subjects reported adverse events. The incidence of adverse events was similar between treatments (85 [91.4%] following oxycodone controlled-release with naloxone compared with 85 [90.4%] following OxyContin®). There were 413 adverse events reported by 85 subjects following treatment with oxycodone controlled-release with naloxone (test) compared with 415 adverse events reported by 85 subjects following treatment with OxyContin® (reference). Pruritus, nausea, dizziness, somnolence, and vomiting were the most frequently reported adverse events following either treatment. These adverse events are consistent with the expected adverse event profile of the opioid analgesic class of drugs represented by oxycodone controlled-release with naloxone and OxyContin®.

Other common adverse events reported following either treatment included euphoria, headache, vasodilatation, and sweating. There were a greater number of subjects reporting vasodilatation, following oxycodone controlled-release with naloxone treatment (23/93, 24.7%) compared with OxyContin® (14/94, 14.9%). After treatment with oxycodone controlled-release with naloxone and OxyContin®, respectively, the following adverse events were reported with similar percentages: headache (23.7%, 22.3%), euphoria (31.2%, 26.6%), and sweating (10.8%, 8.5%).

Overall, no notable differences between the incidence of any specific adverse events reported in Periods 1 and 2 were observed.

Of the events considered at least possibly related to treatment, those reported with the highest incidence following treatment with oxycodone controlled-release with naloxone and OxyContin®, respectively, were: pruritus (52.7%, 50.0%); nausea (47.3%, 36.2%); dizziness (36.6%, 45.7%); somnolence (40.9%, 39.4%); vomiting (33.3%, 30.9%); euphoria (31.2%, 26.6%); vasodilation (23.7%, 14.9%), and headache (19.4%, 19.1%).

Overall, no notable differences between the incidence of adverse events considered at least possibly related to treatment reported in Periods 1 and 2 were observed.

Plasma Concentration-Time Curves

Figure 4:
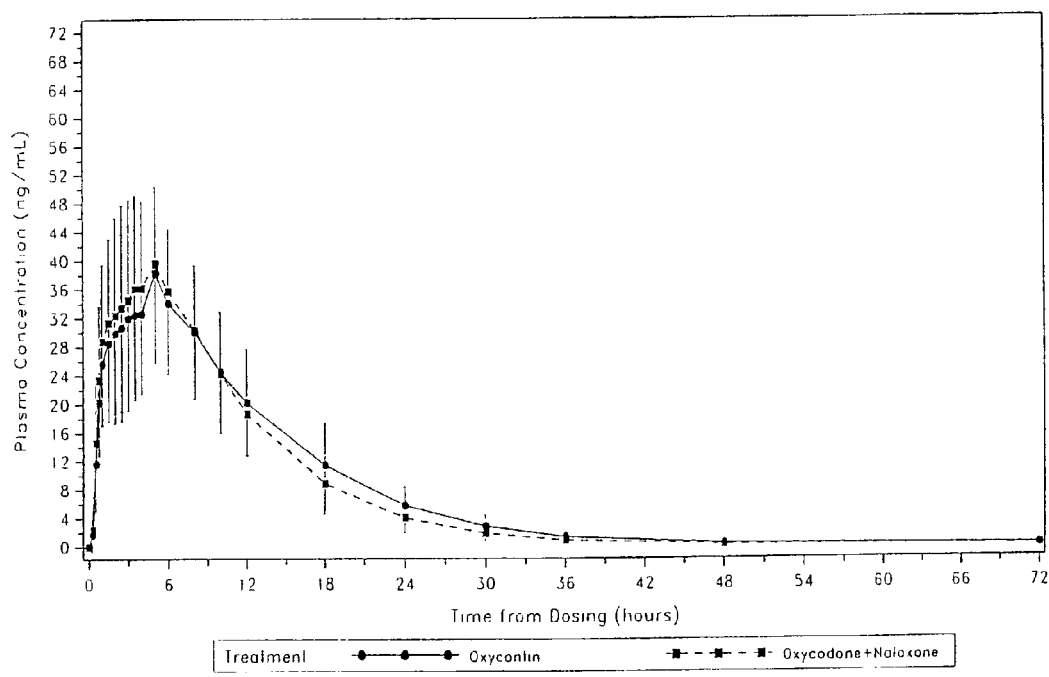
FIG. 4 is a graphical representation of the mean plasma concentrations of oxycodone over time following both treatments in Example 9.

FIG. 4 displays the mean plasma concentrations of oxycodone over time following both treatments.

FIGS. 5 and 6 display the mean observed plasma concentration-time curves for naloxone for all subjects evaluable for safety.

Approximately two-thirds of subjects evaluated had plasma naloxone concentrations that were below the limit of quantitation (BLQ [5 pg/mL]) at the majority of time points. In general, mean plasma naloxone concentrations were low and highly variable. Mean naloxone concentrations over time were <1 pg/mL at all time points. However, there were individual subjects who had plasma levels as high as 26 pg/mL.

Conclusions from the Study

The test treatment (oxycodone controlled-release 40 mg with naloxone 0.85 mg tablet) is bioequivalent to the reference treatment (OxyContin® 40 mg tablet) for oxycodone.

Mean oxycodone $AUC_t$, $AUC_\infty$, $C_{max}$, $t_{max}$, and $t_{1/2}$ values were similar following test and reference treatments, with all values within approximately 10% of each other.

Mean plasma naloxone concentrations were generally low (<1 pg/mL) and highly variable, ranging from approximately 0 to 26 pg/mL in some subjects. Approximately two-thirds of subjects evaluated had plasma naloxone concentrations that were BLQ (5 pg/mL). There was no clinically significant difference in pharmacokinetic data between male and female patients.

Oxycodone controlled-release 40 mg with naloxone 0.85 mg and OxyContin® 40 mg exhibited a similar safety profile. Both were well tolerated by healthy male and female volunteers.

Many other variations of the present invention will be apparent to those skilled in the art and are meant to be within the scope of the claims appended hereto.

What is claimed is:

1. An oral pharmaceutical sustained release composition comprising active ingredients consisting essentially of about 10 mg oxycodone hydrochloride and 0.80 to 0.90 mg naloxone hydrochloride,
   wherein the oxycodone hydrochloride and the naloxone hydrochloride are interdispersed in a matrix comprising a sustained release excipient, and
   the composition, when tested in-vitro by the USP Apparatus I (Basket) method of U.S. Pharmacopoeia XXIV (2000) at 100 rpm in 900 ml simulated gastric fluid (SGF) at 37° C., provides
   a dissolution rate of the oxycodone hydrochloride such that from about 20 to about 60% (by weight) oxycodone hydrochloride is released at 1 hour, from about 40 to about 90% (by weight) oxycodone hydrochloride is released at 4 hours, and greater than about 70% (by weight) oxycodone hydrochloride is released at 12 hours, and
   a dissolution rate of the naloxone hydrochloride which is within about 30% of the dissolution rate of the oxycodone hydrochloride at 1 hour, 4 hours and 12 hours.

2. An oral pharmaceutical sustained release composition comprising active ingredients consisting essentially of about 20 mg oxycodone hydrochloride and 0.80 to 0.90 mg naloxone hydrochloride,
   wherein the oxycodone hydrochloride and the naloxone hydrochloride are interdispersed in a matrix comprising a sustained release excipient, and the composition, when tested in-vitro by the USP Apparatus I (Basket) method of U.S. Pharmacopoeia XXIV (2000) at 100 rpm in 900 ml simulated gastric fluid (SGF) at 37° C., provides a dissolution rate of the oxycodone hydrochloride such that from about 20 to about 60% (by weight) oxycodone hydrochloride is released at 1 hour, from about 40 to about 90% (by weight) oxycodone hydrochloride is released at 4 hours, and greater than about 70% (by weight) oxycodone hydrochloride is released at 12 hours, and a dissolution rate of the naloxone hydrochloride which is within about 30% of the dissolution rate of the oxycodone hydrochloride at 1 hour, 4 hours and 12 hours.

3. An oral pharmaceutical sustained release composition comprising active ingredients consisting essentially of about 40 mg oxycodone hydrochloride and 0.80 to 0.90 mg naloxone hydrochloride in a sustained release dosage form, wherein the oxycodone hydrochloride and the naloxone hydrochloride are interdispersed in a matrix comprising a sustained release excipient, and the composition, when tested in-vitro by the USP Apparatus I (Basket) method of U.S. Pharmacopoeia XXIV (2000) at 100 rpm in 900 ml simulated gastric fluid (SGF) at 37° C., provides a dissolution rate of the oxycodone hydrochloride such that from about 20 to about 60% (by weight) oxycodone hydrochloride is released at 1 hour, from about 40 to about 90% (by weight) oxycodone hydrochloride is released at 4 hours, and greater than about 70% (by weight) oxycodone hydrochloride is released at 12 hours, and a dissolution rate of the naloxone hydrochloride which is within about 30% of the dissolution rate of the oxycodone hydrochloride at 1 hour, 4 hours and 12 hours.

4. The pharmaceutical composition of any one of claims 1-3, wherein the formulation provides effective pain relief for at least 12 hours after steady state oral administration to human patients.

5. The pharmaceutical composition of claim 1, wherein the naloxone hydrochloride has the dissolution rate which is within about 20% of the dissolution rate of the oxycodone hydrochloride at 1 hour, 4 hours and 12 hours.

6. The pharmaceutical composition of claim 1, wherein the naloxone hydrochloride has the dissolution rate which is within about 10% of the dissolution rate of the oxycodone hydrochloride at 1 hour, 4 hours and 12 hours.

7. The pharmaceutical composition of any one of claims 1-3, wherein the dissolution rate of the oxycodone hydrochloride and naloxone hydrochloride is from about 20 to about 60% (by weight) oxycodone hydrochloride and from about 20 to about 60% (by weight) naloxone hydrochloride released at 1 hour; from about 30 to about 75% (by weight) oxycodone hydrochloride and from about 30% to about 75% (by weight) naloxone hydrochloride released at 2 hours; from about 40 to about 90% (by weight) oxycodone hydrochloride and from about 40 to about 90% (by weight) naloxone hydrochloride released at 4 hours; greater than about 60% (by weight) oxycodone hydrochloride and greater than about 60% (by weight) naloxone hydrochloride released at 8 hours; and greater than about 70% (by weight) oxycodone hydrochloride and greater than about 70% (by weight) naloxone hydrochloride released at 12 hours.

8. The pharmaceutical composition of any one of claims 1-3, wherein the dissolution rate of the oxycodone hydrochloride and naloxone hydrochloride is from about 30 to about 60% (by weight) oxycodone hydrochloride and from about 30 to about 60% (by weight) naloxone hydrochloride released at 1 hour; from about 40 to about 70% (by weight) oxycodone hydrochloride and from about 40% to about 70% (by weight) naloxone hydrochloride released at 2 hours; from about 55 to about 90% (by weight) oxycodone hydrochloride and from about 55 to about 90% (by weight) naloxone hydrochloride released at 4 hours; greater than about 70% (by weight) oxycodone hydrochloride and greater than about 70% (by weight) naloxone hydrochloride released at 8 hours; and greater than about 80% (by weight) oxycodone hydrochloride and greater than about 80% (by weight) naloxone hydrochloride released at 12 hours.

9. An oral pharmaceutical sustained release composition comprising active ingredients consisting essentially of about 10 mg to about 40 mg oxycodone or a pharmaceutically acceptable salt thereof and 0.65 to 0.90 mg naloxone or a pharmaceutically acceptable salt thereof, wherein the oxycodone and the naloxone are interdispersed in a matrix comprising a sustained release excipient, and the composition, when tested in-vitro by the USP Apparatus I (Basket) method of U.S. Pharmacopeia XXIV (2000) at 100 rpm in 900 ml simulated gastric fluid (SGF) at 37° C., provides a dissolution rate of the oxycodone such that from about 20 to about 60% (by weight) oxycodone is released at 1 hour, from about 40 to about 90% (by weight) oxycodone is released at 4 hours, and greater than about 70% (by weight) oxycodone is released at 12 hours, and a dissolution rate of the naloxone which is within about 20% of the dissolution rate of the oxycodone at 1 hour, 4 hours and 12 hours.

10. The pharmaceutical composition of any one of claims 1-3, which provides a mean AUC of plasma oxycodone within 80% to 125% of the mean AUC of plasma oxycodone provided by an oxycodone base equivalent amount of oxycodone hydrochloride controlled release reference standard upon single dose administration to a population of human subjects.

11. The pharmaceutical composition of any one of claims 1-3 which provides a mean AUC of plasma oxycodone within 90% to 110% of the mean AUC of plasma oxycodone provided by an oxycodone base equivalent amount of oxycodone hydrochloride controlled release reference standard upon single dose administration to a population of human subjects.

12. The pharmaceutical composition of any one of claims 1-3, which provides a mean AUC of plasma oxycodone within 95% to 105% of the mean AUC of plasma oxycodone provided by an oxycodone base equivalent amount of oxycodone hydrochloride controlled release reference standard upon single dose administration to a population of human subjects.

13. The pharmaceutical composition of any one of claims 1-3, which provides a mean Cmax of plasma naloxone which is at least 50% less than the mean Cmax of plasma naloxone provided by a naloxone base equivalent amount of pentazocine and naloxone hydrochlorides reference standard upon single dose administration to a population of human subjects.

14. The pharmaceutical composition of any one of claims 1-3, which provides a mean Cmax of plasma naloxone which is at least 65% less than the mean Cmax of plasma naloxone provided by a naloxone base equivalent amount of pentazocine and naloxone hydrochlorides reference standard upon single dose administration to a population of human subjects.

15. The pharmaceutical composition of any one of claims 1-3, which provides a mean Cmax of plasma naloxone which is at least 80% less than the mean Cmax of plasma naloxone provided by a naloxone base equivalent amount of pentazocine and naloxone hydrochlorides reference standard upon single dose administration to a population of human subjects.

16. The pharmaceutical composition of any one of claims 1-3, which provides a mean Cmax of plasma naloxone of less than 180 pg/ml upon single dose administration to a population of human subjects.

17. The pharmaceutical composition of any one of claims 1-3, which provides a mean Cmax of plasma naloxone of less than 150 pg/ml upon single dose administration to a population of human subjects.

18. The pharmaceutical composition of any one of claims 1-3, which provides a mean Cmax of plasma naloxone of less than 100 pg/ml upon single dose administration to a population of human subjects.

19. The pharmaceutical composition of any one of claims 1-3, which provides a mean Cmax of plasma naloxone of less than 50 pg/ml upon single dose administration to a population of human subjects.

20. The pharmaceutical composition of any one of claims 1-3, which provides a mean Cmax of plasma naloxone of less than 10 pg/ml upon single dose administration to a population of human subjects.

21. The pharmaceutical composition of any one of claims 1-3, which provides a mean Cmax of plasma naloxone of less than 5 pg/ml upon single dose administration to a population of human subjects.

22. An oral pharmaceutical sustained release composition comprising active ingredients consisting essentially of about 10 mg to about 40 mg oxycodone or a pharmaceutically acceptable salt thereof and 0.65 to 0.90 mg naloxone or a pharmaceutically acceptable salt thereof, wherein the oxycodone and the naloxone are interdispersed in a matrix comprising a sustained release excipient, and the composition provides
   a mean Cmax of plasma naloxone of less than 5 pg/ml upon single dose administration to a population of human subjects,
   and when tested in-vitro by the USP Apparatus I (Basket) method of U.S. Pharmacopoeia XXIV (2000) at 100 rpm in 900 ml simulated gastric fluid (SGF) at 37° C., provides
   a dissolution rate of the oxycodone such that from about 20 to about 60% (by weight) oxycodone is released at 1 hour, from about 40 to about 90% (by weight) oxycodone is released at 4 hours, and greater than about 70% (by weight) oxycodone is released at 12 hours, and
   a dissolution rate of the naloxone which is within about 30% of the dissolution rate of the oxycodone at 1 hour, 4 hours and 12 hours.

23. An oral pharmaceutical sustained release composition comprising active ingredients consisting essentially of about 10-40 mg oxycodone or a pharmaceutically acceptable salt thereof and 0.65 to 0.75 mg naloxone or a pharmaceutically acceptable salt thereof, wherein the oxycodone and the naloxone are interdispersed in a matrix comprising a sustained release excipient, and the composition, when tested in-vitro by the USP Apparatus I (Basket) method of U.S. Pharmacopoeia XXIV (2000) at 100 rpm in 900 ml simulated gastric fluid (SGF) at 37° C., provides
   a dissolution rate of the oxycodone such that from about 20 to about 60% (by weight) oxycodone is released at 1 hour, from about 40 to about 90% (by weight) oxycodone is released at 4 hours, and greater than about 70% (by weight) oxycodone is released at 12 hours, and
   a dissolution rate of the naloxone which is within about 30% of the dissolution rate of the oxycodone at 1 hour, 4 hours and 12 hours.

24. The pharmaceutical composition of claim 22 or 23 comprising 10 mg oxycodone hydrochloride.

25. The pharmaceutical composition of claim 22 or 23 comprising 20 mg oxycodone hydrochloride.

26. The pharmaceutical composition of claim 22 or 23 comprising 40 mg oxycodone hydrochloride.

27. A method of treating pain in a human patient comprising orally administering a pharmaceutical sustained release composition comprising active ingredients consisting essentially of about 10 mg to about 40 mg oxycodone or a pharmaceutically acceptable salt thereof and 0.65 to 0.90 mg naloxone or a pharmaceutically acceptable salt thereof to a patient in pain,
   wherein the oxycodone and the naloxone are interdispersed in a matrix comprising a sustained release excipient, and
   the composition, when tested in-vitro by the USP Apparatus I (Basket) method of U.S. Pharmacopoeia XXIV (2000) at 100 rpm in 900 ml simulated gastric fluid (SGF) at 37° C., provides
   a dissolution rate of the oxycodone such that from about 20 to about 60% (by weight) oxycodone is released at 1 hour, from about 40 to about 90% (by weight) oxycodone is released at 4 hours, and greater than about 70% (by weight) oxycodone is released at 12 hours, and
   a dissolution rate of the naloxone which is within about 30% of the dissolution rate of the oxycodone at 1 hour, 4 hours and 12 hours.

28. The method of claim 27, further comprising orally administering the composition every 12 hours at least until steady state is achieved.

29. A method of preparing a sustained release dosage form comprising incorporating a sustained release excipient and active ingredients consisting essentially of 0.65 to 0.90 mg naloxone or a pharmaceutically acceptable salt thereof and about 10 to about 40 mg oxycodone or a pharmaceutically acceptable salt thereof into a pharmaceutical composition,
   such that the oxycodone and the naloxone become interdispersed in a matrix comprising the sustained release excipient, and the composition, when tested in-vitro by the USP Apparatus I (Basket) method of U.S. Pharmacopoeia XXIV (2000) at 100 rpm in 900 ml simulated gastric fluid (SGF) at 37° C., provides
   a dissolution rate of the oxycodone such that from about 20 to about 60% (by weight) oxycodone is released at 1 hour, from about 40 to about 90% (by weight) oxycodone is released at 4 hours, and greater than about 70% (by weight) oxycodone is released at 12 hours, and
   a dissolution rate of the naloxone which is within about 30% of the dissolution rate of the oxycodone at 1 hour, 4 hours and 12 hours.

30. A method of reducing the parenteral abuse of an oxycodone sustained release product comprising incorporating active ingredients consisting essentially of 0.65 to 0.90 mg naloxone or a pharmaceutically acceptable salt thereof and about 10 to about 40 mg oxycodone or a pharmaceutically acceptable salt thereof into a sustained release product such that the oxycodone and the naloxone become interdispersed in a matrix comprising the sustained release excipient, and the composition, when tested in-vitro by the USP Apparatus I (Basket) method of U.S. Pharmacopoeia XXIV (2000) at 100 rpm in 900 ml simulated gastric fluid (SGF) at 37° C., provides a dissolution rate of the oxycodone such that from about 20 to about 60% (by weight) oxycodone is released at 1 hour, from about 40 to about 90% (by weight) oxycodone is released at 4 hours, and greater than about 70% (by weight) oxycodone is released at 12 hours, and a dissolution rate of the naloxone which is within about 30% of the dissolution rate of the oxycodone at 1 hour, 4 hours and 12 hours.

31. A method of treating pain comprising administering a pharmaceutical sustained release composition comprising active ingredients consisting essentially of about 10 mg oxycodone hydrochloride and 0.65 to 0.90 mg naloxone or a pharmaceutically acceptable salt thereof, and thereafter increasing the dosage by administering a pharmaceutical sustained release composition comprising about 20 mg oxycodone hydrochloride and 0.65 to 0.90 mg naloxone or a pharmaceutically acceptable salt thereof, wherein, in each composition, the oxycodone hydrochloride and the naloxone are interdispersed in a matrix comprising a sustained release excipient, and each composition, when tested in-vitro by the USP Apparatus I (Basket) method of U.S. Pharmacopoeia XXIV (2000) at 100 rpm in 900 ml simulated gastric fluid (SGF) at 37° C., provides a dissolution rate of the oxycodone hydrochloride such that from about 20 to about 60% (by weight) oxycodone hydrochloride is released at 1 hour, from about 40 to about 90% (by weight) oxycodone hydrochloride is released at 4 hours, and greater than about 70% (by weight) oxycodone hydrochloride is released at 12 hours, and a dissolution rate of the naloxone which is within about 30% of the dissolution rate of the oxycodone hydrochloride at 1 hour, 4 hours and 12 hours.

32. A method of treating pain comprising administering a pharmaceutical sustained release composition comprising active ingredients consisting essentially of about 20 mg oxycodone hydrochloride and 0.65 to 0.90 mg naloxone or a pharmaceutically acceptable salt thereof, and thereafter increasing the dosage by administering a pharmaceutical sustained release composition comprising about 40 mg oxycodone hydrochloride and 0.65 to 0.90 mg naloxone or a pharmaceutically acceptable salt thereof, wherein, in each composition, the oxycodone hydrochloride and the naloxone are interdispersed in a matrix comprising a sustained release excipient, and each composition, when tested in-vitro by the USP Apparatus I (Basket) method of U.S. Pharmacopoeia XXIV (2000) at 100 rpm in 900 ml simulated gastric fluid (SGF) at 37° C., provides a dissolution rate of the oxycodone hydrochloride such that from about 20 to about 60% (by weight) oxycodone hydrochloride is released at 1 hour, from about 40 to about 90% (by weight) oxycodone hydrochloride is released at 4 hours, and greater than about 70% (by weight) oxycodone hydrochloride is released at 12 hours, and a dissolution rate of the naloxone which is within about 30% of the dissolution rate of the oxycodone hydrochloride at 1 hour, 4 hours and 12 hours.

33. A method of treating pain comprising administering a pharmaceutical sustained release composition comprising active ingredients consisting essentially of about 10 mg oxycodone hydrochloride and 0.65 to 0.90 mg naloxone or a pharmaceutically acceptable salt thereof and thereafter increasing the dosage by administering a pharmaceutical sustained release composition comprising about 20 mg oxycodone hydrochloride and 0.65 to 0.90 mg naloxone or a pharmaceutically acceptable salt thereof, and thereafter increasing the dosage by administering a pharmaceutical sustained release composition comprising about 40 mg oxycodone hydrochloride and 0.65 to 0.90 mg naloxone or a pharmaceutically acceptable salt thereof, wherein, in each composition, the oxycodone hydrochloride and the naloxone are interdispersed in a matrix comprising a sustained release excipient, and each composition, when tested in-vitro by the USP Apparatus I (Basket) method of U.S. Pharmacopoeia XXIV (2000) at 100 rpm in 900 ml simulated gastric fluid (SGF) at 37° C., provides a dissolution rate of the oxycodone hydrochloride such that from about 20 to about 60% (by weight) oxycodone hydrochloride is released at 1 hour, from about 40 to about 90% (by weight) oxycodone hydrochloride is released at 4 hours, and greater than about 70% (by weight) oxycodone hydrochloride is released at 12 hours, and a dissolution rate of the naloxone which is within about 30% of the dissolution rate of the oxycodone hydrochloride at 1 hour, 4 hours and 12 hours.

34. A kit for the treatment of pain comprising:

a container comprising at least one formulation comprising active ingredients consisting essentially of about 10 to about 40 mg oxycodone or a pharmaceutically acceptable salt thereof in sustained release form and 0.65 to 0.90 mg naloxone or a pharmaceutically acceptable salt thereof; the formulation, when tested in-vitro by the USP Apparatus I (Basket) method of U.S. Pharmacopoeia XXIV (2000) at 100 rpm in 900 ml simulated gastric fluid (SGF) at 37° C., provides a dissolution rate of the oxycodone such that from about 20 to about 60% (by weight) oxycodone is released at 1 hour, from about 40 to about 90% (by weight) oxycodone is released at 4 hours, and greater than about 70% (by weight) oxycodone is released at 12 hours, and a dissolution rate of the naloxone which is within about 30% of the dissolution rate of the oxycodone at 1 hour, 4 hours and 12 hours; and an indicia indicating the use of said formulation.

35. The kit of claim 34, wherein said indicia indicates that said use is to reduce the parenteral abuse of said formulation.

36. The pharmaceutical composition of claim 1, wherein the composition provides sustained release of the naloxone hydrochloride.

37. The pharmaceutical composition of claim 2, wherein the composition provides sustained release of the naloxone hydrochloride.

38. The pharmaceutical composition of claim 3, wherein the composition provides sustained release of the naloxone hydrochloride.

\* \* \* \* \*